United States Patent
Blankenstein et al.

(10) Patent No.: US 9,133,264 B2
(45) Date of Patent: Sep. 15, 2015

(54) EPITOPE-TAG SURFACE EXPRESSED PROTEINS AND NUCLEIC ACIDS THEREOF

(75) Inventors: Thomas Blankenstein, Berlin (DE); Wolfgang Uckert, Berlin (DE); Elisa Kieback, Berlin (DE); Jehad Charo, Berlin (DE)

(73) Assignee: MAX-DELBRUCK-CENTRUM FUR MOLEKULARE MEDIZIN (MDC) BERLIN-BUCH, Berlin (DE)

( * ) Notice: Subject to any disclaimer, the term of this patent is extended or adjusted under 35 U.S.C. 154(b) by 1538 days.

(21) Appl. No.: 12/373,362

(22) PCT Filed: Jun. 22, 2007

(86) PCT No.: PCT/EP2007/005541
§ 371 (c)(1),
(2), (4) Date: Nov. 2, 2009

(87) PCT Pub. No.: WO2008/006458
PCT Pub. Date: Jan. 17, 2008

(65) Prior Publication Data
US 2010/0104556 A1    Apr. 29, 2010

(30) Foreign Application Priority Data
Jul. 13, 2006 (EP) .................................. 06014606

(51) Int. Cl.
| | |
|---|---|
| C07K 14/47 | (2006.01) |
| C07K 14/705 | (2006.01) |
| C07K 14/725 | (2006.01) |
| C07K 19/00 | (2006.01) |
| C07H 21/04 | (2006.01) |
| C12N 15/09 | (2006.01) |
| C12N 15/63 | (2006.01) |
| C12P 21/02 | (2006.01) |
| A61K 38/17 | (2006.01) |
| C12N 15/62 | (2006.01) |
| C12N 15/79 | (2006.01) |
| A61K 38/00 | (2006.01) |
| A61K 48/00 | (2006.01) |
| A61K 35/12 | (2015.01) |
| A61K 39/00 | (2006.01) |

(52) U.S. Cl.
CPC ........... *C07K 14/7051* (2013.01); *A61K 38/177* (2013.01); *C12N 15/62* (2013.01); *C12N 15/79* (2013.01); *A61K 38/00* (2013.01); *A61K 48/00* (2013.01); *A61K 2035/124* (2013.01); *A61K 2039/5158* (2013.01); *C07K 2319/20* (2013.01); *C07K 2319/21* (2013.01); *C07K 2319/23* (2013.01); *C07K 2319/40* (2013.01); *C07K 2319/41* (2013.01); *C07K 2319/43* (2013.01)

(58) Field of Classification Search
None
See application file for complete search history.

(56) References Cited

U.S. PATENT DOCUMENTS

| | | | |
|---|---|---|---|
| 4,703,004 A | 10/1987 | Hopp et al. | |
| 4,851,341 A | 7/1989 | Hopp et al. | |
| 4,980,281 A | 12/1990 | Housey | |
| 5,266,464 A | 11/1993 | Housey | |
| 5,587,455 A | 12/1996 | Berger et al. | |
| 5,688,655 A | 11/1997 | Housey | |
| 5,696,237 A | 12/1997 | Fitzgerald et al. | |
| 5,767,260 A | 6/1998 | Whitlow et al. | |
| 5,856,456 A | 1/1999 | Whitlow et al. | |
| 5,914,254 A | 6/1999 | Mascarenhas et al. | |
| 5,925,333 A | 7/1999 | Krieger et al. | |
| 5,981,177 A | 11/1999 | Demirjian et al. | |
| 5,994,104 A | 11/1999 | Anderson et al. | |
| 6,491,908 B1 | 12/2002 | Rosenberg | |
| 6,576,428 B1 | 6/2003 | Assenmacher et al. | |
| 2003/0152559 A1* | 8/2003 | Yang et al. ................. | 424/93.21 |

FOREIGN PATENT DOCUMENTS

| | | |
|---|---|---|
| EP | 1188825 | 3/2002 |
| WO | 98/36087 | 8/1998 |
| WO | 98/39482 | 9/1998 |
| WO | 99/18129 | 4/1999 |
| WO | 02/054065 | 7/2002 |
| WO | 03/095663 | 11/2003 |
| WO | WO-2004048410 A2 * | 6/2004 |

OTHER PUBLICATIONS

Kaufman et al. Transgenic analysis of a 100-kb human beta-globin cluster-containing DNA fragment propagated as a bacterial artificial chromosome. Blood 94(9): 3178-3184, 1999.*

Kieback et al. A safeguard eliminates T cell receptor gene-modified autoreactive T cells after adoptive transfer. Proc Natl Acad Sci USA 105(2): 623-628, 2008.*

McBurney et al. Evidence for repeat-induced gene silencing in cultured mammalian cells: inactivation of tandem repeats of transfected genes. Exp Cell Res 274: 1-8, 2002.*

Phillips, A.J. The challenge of gene therapy and DNA delivery. J Pharm Pharmacol 53: 1169-1174, 2001.*

Wang et al. Rapid analysis of gene expression (RAGE) facilitates universal expression profiling. Nucleic Acids Research 27(23): 4609-4618, 1999.*

Williams et al. BMC Biotechnol 5:17, 2005.*

Elgert, K. Immunology: Understanding the immune system. New York: Wiley-Liss, 1996;; pp. 176-179.*

(Continued)

*Primary Examiner* — Bridget E Bunner
(74) *Attorney, Agent, or Firm* — Nixon Peabody LLP; Mark J. FitzGerald

(57) ABSTRACT

The present invention relates to a method for selecting a host cell population expressing a functional fusion protein comprising at least one epitope-providing amino acid sequence (epitope-tag) and the amino acid sequence of a protein that is expressed on the surface of said host cell. Preferably, the amino acid sequence comprises an alpha or beta chain of a T-cell receptor. The present invention further relates to uses of said functional T-cell receptor (TCR) alpha or beta chain fusion protein in medicine, in particular in adoptive transfer.

12 Claims, 8 Drawing Sheets

(56) References Cited

OTHER PUBLICATIONS

Fuschiotti et al. Analysis of the TCR alpha-chain rearrangement profile in human T lymphocytes. Mol Immunol 44: 3380-3388, 2007.*

Klein et al. Diversity and structure of human T-cell receptor alpha-chain variable region genes. Proc Natl Acad Sci USA 84: 6884-6888, 1987.*

Berger, C. et al., Blood, 103(4):1261-9 (2004). "Pharmacologically regulated Fas-mediated death of adoptively transferred T cells in a nonhuman primate model."

Bonini, C. et al., Science, 276(53 19):1719-24 (1997). "HSV-TK gene transfer into donor lymphocytes for control of allogeneic graft-versus-leukemia."

Cobbold, M. et al., J Exp Med., 202(3):379-86 (2005). "Adoptive transfer of cytomegalovirus-specific CTL to stem cell transplant patients after selection by HLA-peptide tetramers."

Heemskerk, M.H.M. et al., Blood, 98(11, part 1):701a (2001). "Modification of non-HLA restricted gammadelta T cells into antigen specific HLA restricted killer T cells by TCRalphabeta gene transfer."

Hodi, F.S., et al., Adv Immunol., 90:341-68 (2006). "Combinatorial cancer immunotherapy."

Ishii, Y. et al., J Immunol., 156(5):1735-42 (1996). "Biochemical characterization of antigen-specific glycosylation-inhibiting factor from antigen-specific suppressor T cells. II. The 55-kDa glyosylation-inhibiting factor peptide is a derivative of TCR alpha-chain and a subunit of antigen-specific glycosylation-inhibiting factor."

Karakhanova, S. et al., J Immunother., 29(3):336-49 (2006). "Highly efficient expansion of human CD4+CD25+ regulatory T cells for cellular immunotherapy in patients with graft-versus-host disease."

Lu et al., J. Org. Chem., 46:3433-3436 (1981). "Improved synthesis of 4-alkoxybenzyl alcohol resin."

Martin, E.W., Remington's Pharmaceutical Sciences, Mack Publishing Co., Easton, Pa., 15th Edition (1975). Synopsis Only.

Nag, B. et al., J. Immunol. Methods, 169(2):273-85 (1994). "Separation of complexes of major histocompatibility class II molecules and known antigenic peptide by metal chelate affinity chromatography."

Pellicci, D.G. et al., J Immunol Methods, 246(1-2):149-63 (2000). "Expression and purification of antigenically active soluble derivatives of the heterodimeric and homodimeric forms of the mouse CD8 lymphocyte membrane glycoprotein."

Schleicher, U. et al., Journal of Immunological Methods, 246(1-2):165-174 (2000). "A stable marker for specific T-cells: a TCR alpha/green fluorescent protein (GFP) fusion protein reconstitutes a functionally active TCR complex."

Van Der Veken, L.T. et al., Blood, 102(11):747a (2003). "Retroviral transfer of an HLA class II restricted T cell receptor (TCR) to CD4+ or CD8+ T cells results in transfer of T cell specificity with all effector functions displayed by the TCR-receiving T cell."

Van Der Veken, L.T. et al., Cancer Research, 66(6):3331-3337 (2006). "Alpha beta T-cell receptor engineered gamma delta T cells mediate effective antileukemic reactivity.", Abstract only.

Graham A. Bentley et al., "The Structure of the T Cell Antigen Receptor", Annu. Rev. Immunol., 1996, 563-590, 14, Annual Reviews, Inc.

K. Christopher Garcia et al., "Anαβ T Cell Receptor Structure at 2.5 Å and its Orientation in the TCR-MHC Complex", Science AAS, Oct. 11, 1996, 209-219, vol. 274, No. 5285, American Association for the Advancement of Science.

W.R. Hein, "Structural and Functional Evolution of the Extracellular Regions of T Cell Receptors", Seminars in Immunology, 1994, 361-372, vol. 6, Basel Institute for Immunology, Switzerland.

Yasunobu Yoshikai et al., "Sequences and Repertoire of Human T Cell Receptor α Chain Variable Region Genes in Mature T Lymphocytes", J. Exp. Med., Jul. 1986, 90-103, vol. 164, The Rockefeller University Press.

Abul K. Abbas et al., "Cellular and Molecular Immunology", Library of Congress Cataloging-in-Publication Data, 1991, 138-167, W.B. Saunders Company, United States of America.

George Johnson et al., "The Kabat Database and a Bioinformatics Example", Methods in Molecular Biology, vol. 248, 11-25, Humana Press Inc., Totowa, New Jersey, 2004.

\* cited by examiner

I.  II.

A

B

C

D a b c d

EPITOPE-TAG SURFACE EXPRESSED PROTEINS AND NUCLEIC ACIDS THEREOF

CROSS-REFERENCE TO RELATED APPLICATIONS

This application is a 35 U.S.C. §371 National Stage of International Application No. PCT/EP2007/005541 filed on Jun. 22, 2007, which designates the United States, and which claims the benefit under 35 U.S.C. §119 (a) of European Application No. 06014606.5 filed on Jul. 13, 2006 the contents of which are incorporated by reference herein in its entirety.

Sequence Listing

The instant application contains a Sequence Listing which has been submitted in ASCII format via EFS-Web and is hereby incorporated by reference in its entirety. Said ASCII copy, created on Jun. 4, 2012, is named 54451645.txt and is 6,705 bytes in size.

The present invention relates to a method for selecting a host cell population expressing a functional fusion protein comprising at least one epitope-providing amino acid sequence (epitope-tag) and the amino acid sequence of a protein that is expressed on the surface of said host cell. Preferably, the amino acid sequence comprises an alpha or beta chain of a T-cell receptor. The present invention further relates to uses of said functional T-cell receptor (TCR) alpha or beta chain fusion protein in medicine, in particular in adoptive transfer.

Cytotoxic T lymphocytes (CTLs) specifically recognize foreign antigens presented on their target cells via MHC class I molecules. Their specificity is determined by the T cell receptor (TCR) expressed on the surface of the lymphocyte. In vitro modification of a population of CTLs with TCR genes can provide these cells with a new specificity. This enables them to recognize and eliminate their target cells after adoptive transfer.

The therapeutic efficacy of adoptively transferred cytotoxic T cells (CTL) has been demonstrated in first human tumor models and for viral diseases using allogeneic bone marrow transplantation. However, this possibility is restricted by the difficulty to reproducibly generate sufficient amounts of specific T cells in vitro. Recent gene therapy approaches include the genetic engineering of T cells to transfer antigen specificity.

However, it was shown that activation of the transgenic TCR by recognition of target antigens will also allow effector functions via the endogenous TCR. If the endogenous TCR is self-reactive, the therapy might lead to auto-immune side effects which cannot be tolerated. In the same way, pairing of a transgenic TCR chain with a chain of the endogenous TCR can result in a number of mixed TCR heterodimers with unpredictable specificity that may have auto-reactive potential.

Despite the possibility to retrovirally transduce functional TCR alpha and beta chains to peripheral T lymphocytes and to redirect T cell activity towards antigen recognition by the introduced TCR, there are several safety concerns with this approach. One possible side-effect of TCR gene transfer could be the induction of autoimmunity since the target antigen is often a self antigen. Indeed, the majority of tumor-associated antigens that have been identified in human are self-antigens, that are over-expressed in tumors, but also occur in normal tissues, raising the problem that adoptively transferred T cells could cause autoimmunity. The second potential mechanism to induce autoimmunity might result in the modification of ignorant self-specific T cells by TCR gene transfer in a way that these T cells might become auto-aggressive after triggering through their transduced exogenous TCR. For these reason redirected T cells obtained by TCR gene transfer have to be carefully evaluated with respect to both efficacy and safety and have to be eradicated if this is necessary.

In order to avoid these problems with adoptive transfer, currently mainly the following options are employed in order to eliminate adoptively transferred T cells.

1) Suicide gene/prodrug systems (e.g. herpes simplex virus thymidine kinase, HSV-TK) have been used as safety modality in T lymphocytes and hematopoietic stem cells in clinical applications (HSV-TK gene transfer into donor lymphocytes for control of allogeneic graft-versus-leukemia", Bonini C, Ferrari G, Verzeletti S, Servida P, Zappone E, Ruggieri L, Ponzoni M, Rossini S, Mavilio F, Traversari C, Bordignon C., Science. 1997 Jun. 13; 276(53 19): 1719-24);
2) The application of apoptosis-inducing molecules (e.g. caspases, FADD, Fas) has been described as a possible mechanism to deplete adoptively transferred T lymphocytes (Pharmacologically regulated Fas-mediated death of adoptively transferred T cells in a nonhuman primate model", Berger C, Blau C A, Huang M L, Iuliucci J D, Dalgarno D C, Gaschet J, Heimfeld S, Clackson T, Riddell S R., Blood. 2004 Feb. 15; 103(4):1261-9. Epub 2003 Oct. 16);
3. The use of corticosteroids as local therapy.
4. Chemotherapy for the elimination of T-cells.

Nevertheless, all these methods suffer from disadvantages, for example, T cells are difficult to transduce and extended ex vivo culturing should be avoided, which would be required for complex genetic systems to be introduced. Furthermore, escape mechanisms such as down-regulation or silencing of the suicide gene have been observed for GSV-TK. This leads to a population of cells which is resistant to drug treatment and cannot be eliminated. Finally, corticosteroid and prodrug therapy have severe side effects. Furthermore, all of these strategies require introduction of at least one additional gene into T cells. Retroviral vectors—the most commonly used system to transduce T cells—only have a limited transgene capacity.

Considering the size of the TCRα- and TCRβ-chain genes it is unlikely that vectors that carry an additional gene can efficiently transduce T cells. Hence, PBLs necessarily have to be independently transduced with a TCR and a second gene encoding vector. This increases the number of retroviral integrations into the host cell genome, and thus the risk of insertional mutagenesis. Also, the purification and analysis steps needed to ensure that all TCR-redirected cells express the gene that allows the execution of cell elimination will prolong the in vitro culture time of PBLs and finally decrease their functionality.

Nag et al. (Nag B, Mukku P V, Arimilli S, Kendrick T, Deshpande S V, Sharma S D. Separation of complexes of major histocompatibility class II molecules and known antigenic peptide by metal chelate affinity chromatography. J Immunol Methods. 1994 Mar. 10; 169(2):273-85.) describe the problem that no simple method with acceptable recovery exists for separation of complexes of a known antigenic epitope and MHC class II from empty MHC class II and complexes of MHC class II and endogenously bound peptide, and propose a one step metal chelate affinity chromatography method to purify complexes of MHC class II and antigenic peptide of known composition. Complexes of human HLA- DR2 (DRB1*1501/DRB5*0101) and a peptide analog from human myelin basic protein MBP(84-102) containing a 6 histidine tag (6×His) (SEQ ID NO: 3)and a tyrosine residue at the N-terminus end [6×His-MBP(83-102)Y83] ('6 ×HIS' disclosed as SEQ ID NO: 3)were prepared and purified.

Cobbold et al. (Cobbold M, Khan N, Pourgheysari B, Tauro S, McDonald D, Osman H, Assenmacher M, Billingham L, Steward C, Crawley C, Olavarria E, Goldman J, Chakraverty R, Mahendra P, Craddock C, Moss P A. Adoptive transfer of cytomegalovirus-specific CTL to stem cell transplant patients after selection by HLA-peptide tetramers. J Exp Med. 2005 Aug. 1; 202(3):379-86) describe the adoptive transfer of donor-derived CMV-specific CD8+ T cell clones and the purification of CMV-specific CD8+ T cells from the blood of stem cell transplant donors using staining with HLA-peptide tetramers followed by selection with magnetic beads.

Ishii et al. (Ishii Y, Nakano T, Ishizaka K. Biochemical characterization of antigen-specific glycosylation-inhibiting factor from antigen-specific suppressor T cells. II. The 55-kDa glycosylation-inhibiting factor peptide is a derivative of TCR alpha-chain and a subunit of antigen-specific glycosylation-inhibiting factor. J. Immunol. 1996 Mar. 1; 156(5): 1735-42.) describe a unique TCR alpha-chain derived from the OVA-specific Ts hybridoma, 231F1, and attempts to transfect the TCR-alpha cDNA into a TCR-alpha-, TCR-beta+ T cell line. However, the stable transfectant failed to release a peptide with the TCR-alpha determinant upon stimulation with anti-CD3. In order to obtain evidence for a relationship between a 55-kDa peptide as described and the TCR alpha-chain, a cDNA of the TCR alpha-chain with a histidine tag was introduced into 231F1 cells. The 55 kDa GIF peptide formed by stable transfectants of the TCR-alpha-tag cDNA bound to Ni+-nitrilotriacetic acid-agarose. The results indicate that the OVA-specific GIF consists of the TCR-alpha+ 55-kDa GIF and another peptide with TCR-beta determinant. No adoptive transfer or analysis thereof is described.

Pellicci et al. (Pellicci D G, Kortt A A, Sparrow L G, Hudson P J, Sorensen H V, Davis S J, Classon B J. Expression and purification of antigenically active soluble derivatives of the heterodimeric and homodimeric forms of the mouse CD8 lymphocyte membrane glycoprotein. J Immunol Methods. 2000 Dec. 1; 246(1-2):149-63.) describe an expression strategy for production of soluble CD8alphaalpha and CD8alphabeta extracellular domains for use in ligand binding studies. In order to resolve the CD8alphaalpha homodimer from the CD8alphabeta heterodimer, affinity chromatographic techniques specific for the CD8beta subunit were employed. The inclusion of a hexahistidine tag (SEQ ID NO: 3) at the C-terminus of CD8beta enabled affinity purification of soluble CD8alphabeta (and sCD8alphaalpha) under neutral conditions, yielding recombinant protein with the correct stoichiometry and full antigenic activity. The method is proposed as useful for production of other soluble recombinant heterodimeric receptor proteins whose antigenicity is affected by denaturation during immunoaffinity purification.

U.S. Pat. No. 6,756,215 relates to functionalized TGF-beta fusion proteins that display substantial native TGF-beta family protein function while also having an additional functionality conveyed by the addition of a functionalizing peptide domain. Such functionalizing peptide domain can be a tag peptide (e.g., an epitope tag, a purification tag, a molecular size differentiation tag, etc.) or a passenger or targeting protein. Also described are methods of making these fusions, as well as methods of using them for diagnosis and diagnosis of various conditions, in measuring and monitoring levels of the fusion molecule in experimental systems and subjects, and in measuring and detecting receptor proteins.

The object of the present invention is to provide a strategy in order to select and/or eliminate cells that have been recombinantly provided with proteins that are to expressed on the surface of said cells, and, preferably, adoptively transferred TCR-engineered T cells in vivo and or in vitro. Said elimination should be effective and, at the same time, should leave the respective recombinant proteins, e.g. TCRs, functional. Other objects of the present invention are readily derivable for the person of skill upon studying the description of the present invention as provided herein.

In one preferred aspect thereof, the object of the present invention is solved by a method for selecting a host cell population expressing a fusion protein selected from the group consisting of a) a functional fusion protein comprising at least one epitope-providing amino acid sequence (epitope-tag), and the amino acid sequence of a protein that is expressed on the surface of said host cell, wherein said epitope-tag is selected from i) an epitope-tag added to the N- and/or C-terminus of said protein, ii) an epitope-tag inserted into a region of said protein, and an epitope-tag replacing a number of amino acids in said protein, b) a fusion protein comprising i) at least one epitope-providing amino acid sequence (epitope-tag), and ii) the amino acid sequence of an alpha or beta chain of a TCR, wherein said epitope-tag is selected from an epitope-tag added to the N- and/or C-terminus of said alpha and/or beta chain, an epitope-tag inserted into a constant region of said alpha and/or beta chain, and an epitope-tag replacing a number of amino acids in a constant region of said alpha and/or beta chain, and c) a TCR comprising at least one fusion protein according to b) on the surface of the host cell, comprising contacting host cells in a sample with a binding agent that immunologically binds to the epitope-tag, and selection of said host cells based on said binding.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Epitope tags add a known epitope (antibody binding site) on the subject protein, to provide binding of a known and often high-affinity antibody, and thereby allowing one to specifically identify and track the tagged protein that has been added to a living organism or to cultured cells. Examples of epitope tags include the myc, T7, GST, GFP, HA (hemagglutinin) and FLAG tags. The first four examples are epitopes derived from existing molecules. In contrast, FLAG is a synthetic epitope tag designed for high antigenicity (see, e.g., U.S. Pat. Nos. 4,703,004 and 4,851,341). The myc tag was used in some particular examples disclosed herein because high quality reagents are available to be used for its detection. Epitope tags can of course have one or more additional functions, beyond recognition by an antibody.

According to the invention, a protein that is expressed on the surface of said host cell can be any recombinant protein that is displayed, at least in part, on the outside of a cell. Examples for such a cell surface protein are receptors, such as cell signaling receptors, T-cell receptors, cell adhesion molecules, and molecules such as CD3, CD8, or other CD-cell surface molecules.

Preferred is a method according to the present invention, wherein said host cell is selected from hematopoietic cells, such as NK cells or tumor cells, T-cells and T-cell-precursor cells and non-pluripotent stem cells.

Further preferred is a method according to the present invention, wherein said epitope-tag has a length of between 6 to 15 amino acids, preferably 9 to 11 amino acids. Even more preferred is a method according to the present invention, wherein said fusion protein comprises two or more epitope-tags, either spaced apart or directly in tandem. Embodiments of the method can contain 2, 3, 4, 5 or even more epitope-tags, as long as the fusion protein maintains its biological activity/activities ("functional").

Preferred is a method according to the present invention, wherein said epitope-tag is selected from a myc-tag, FLAG-tag, T7-tag, HA (hemagglutinin)-tag, His-tag, S-tag, GST-tag, and GFP-tag. The sequences of these tags are described in the literature and well known to the person of skill in art.

In the context of the present invention, an "immunologically binding" is a non-covalent form of attaching between an epitope of an antigen (in the present case the epitope-tag) and the antigen-specific part of an antibody or fragment thereof. Antibodies are preferably monoclonal and must be specific for the respective epitope tag(s) as used. Antibodies include murine, human and humanized antibodies. Antibody fragments are known to the person of skill and include, amongst others, single chain Fv antibody fragments (scFv fragments) and Fab-fragments. The antibodies can be produced by regular hybridoma and/or other recombinant techniques. Many antibodies are commercially available.

Further preferred is a method according to the present invention which further comprises an enriching of the host cells based on said binding and/or an inactivation of the host cells based on said binding. In one preferred example, enriching can be done by a method assay comprising binding to an antibody or fragment thereof that is attached to a solid surface, such as a resin in a column. Inactivation of said cells is usually and preferably performed by binding of the tag to an antibody or fragment thereof, and subsequent inactivation, preferably killing, of the bound cell by cellular mechanisms. It is also possible to couple the antibody or fragment thereof to a cytotoxic moiety, such as a toxin or other cytotoxic substance. These techniques and respective antibody-constructs are also known to the person of skill.

The construction of fusion proteins from domains of known proteins, or from whole proteins or proteins and peptides, is well known. In general, a nucleic acid molecule that encodes the desired protein and/or peptide portions are joined using genetic engineering techniques to create a single, operably linked fusion oligonucleotide. Appropriate molecular biological techniques may be found in Sambrook et al. (1989). Examples of genetically engineered multi-domain proteins, including those joined by various linkers, and those containing peptide tags, can be found in the following patent documents: U.S. Pat. No. 5,994,104 ("Interleukin-12 fusion protein"); U.S. Pat. No. 5,981,177 ("Protein fusion method and construction"); U.S. Pat. No. 5,914,254 ("Expression of fusion polypeptides transported out of the cytoplasm without leader sequences"); U.S. Pat. No. 5,856,456 ("Linker for linked fusion polypeptides"); U.S. Pat. No. 5,767,260 ("Antigen-binding fusion proteins"); U.S. Pat. No. 5,696,237 ("Recombinant antibody-toxin fusion protein"); U.S. Pat. No. 5,587,455 ("Cytotoxic agent against specific virus infection"); U.S. Pat. No. 4,851,341 ("Immunoaffinity purification system"); U.S. Pat. No. 4,703,004 ("Synthesis of protein with an identification peptide"); and WO 98/36087 ("Immunological tolerance to HIV epitopes").

The placement of the functionalizing peptide portion (epitope-tag) within the subject fusion proteins is influenced by the activity of the functionalizing peptide portion and the need to maintain at least substantial fusion protein, such as TCR, biological activity in the fusion. Two methods for placement of a functionalizing peptide are illustrated in the detailed examples: N-terminal, and at a location within a protein portion that exhibits amenability to insertions. Though these are not the only locations in which functionalizing peptides can be inserted, they serve as good examples, and will be used as illustrations. Other appropriate insertion locations can be identified by inserting test peptide encoding sequences (e.g., a sequence encoding the FLAG peptide) into a TCR construct at different locations, then assaying the resultant fusion for TCR biological activity and functionalizing peptide activity, using assays that are appropriate for the specific portions used to construct the fusion. The activity of TCR proteins can be measured using any of various known techniques, including those method described herein.

The object of the present invention is furthermore solved by a functional T-cell receptor (TCR) alpha or beta chain fusion protein, comprising: a) at least one epitope-providing amino acid sequence (epitope-tag) as described herein, and b) the amino acid sequence of an alpha or beta chain of a TCR, wherein said epitope-tag is selected from a) an epitope-tag added to the N- and/or C-terminus of said alpha and/or beta chain, b) an epitope-tag inserted into a constant region of said alpha and/or beta chain, and c) an epitope-tag replacing a number of amino acids in a constant region of said alpha and/or beta chain.

In the context of the present invention, a "functional" T-cell receptor (TCR) alpha or beta chain fusion protein shall mean an alpha or beta chain fusion protein that, although the chain includes the eptiope-tag and/or has a tag attached to it, maintains at least substantial fusion protein biological activity in the fusion. In the case of the alpha and beta chains of a TCR, this shall mean that both chains remain able to form a T-cell receptor (either with a non-modified alpha or beta chain or with another inventive fusion protein alpha or beta chain) which exerts its biological function, in particular binding to the specific peptide-MHC complex of said TCR, and/or functional signal transduction upon peptide activation.

Preferred is a functional T-cell receptor (TCR) alpha or beta chain fusion protein according to the present invention, wherein said epitope-tag has a length of between 6 to 15 amino acids, preferably 9 to 11 amino acids. Even more preferred is a functional T-cell receptor (TCR) alpha or beta chain fusion protein according to the present invention, wherein said T-cell receptor (TCR) alpha or beta chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional T-cell receptor (TCR) alpha or beta chain fusion protein according to the present invention, wherein said epitope-tag is selected from a myc-tag, FLAG-tag, T7-tag, HA (hemagglutinin)-tag, His-tag, S-tag, GST-tag, and GFP-tag. The sequences of these tags are described in the literature and well known to the person of skill in art.

In a particularly preferred embodiment of the functional T-cell receptor (TCR) alpha or beta chain fusion protein according to the present invention, said fusion protein is selected from two myc-tag sequences that are attached to the N-terminus of an alpha TCR-chain and/or 10 amino acids of a protruding loop region in the beta-chain constant domain being exchanged for the sequence of two myc-tags.

In a preferred embodiment of the present invention, the inventors inserted an amino acid sequence that corresponds to a part of the myc protein (myc-tag) at several reasonable sites into the structure of a T cell receptor and transduced this modified receptor into T cells (see examples below). By introducing a tag into the TCR structure, it is possible to deplete the modified cells by administering the tag-specific antibody to the patient.

The present in provides several advantages, compared to other methods that are currently available in adoptive transfer:
1. No further gene has to be transferred into the TCR-gene modified T cell. This is of importance, because T cells are difficult to transduce and extended ex vivo culturing should be avoided.
2. Escape mechanisms such as down-regulation or silencing of the suicide gene have been reported for GSV-TK. This leads to a population of cells which is resistant to drug treatment and cannot be eliminated. Down-regulation or silencing of the tagged inventive TCR due to escape mechanisms will lead to inactivation of the transferred cells as lacking expression of the TCR prevents T cell stimulation.
3. TCR-myc-tag gene modified T cells can be ex vivo enriched for those cells showing a high level of transgene expression. Thus, only biologically active cells can be selected and used for adoptive transfer.
3. Corticosteroid and prodrug therapy have severe side effects, which will be avoided.
4. Specificity of the tag and its high efficacy.

Another preferred aspect of the present invention relates to a functional TCR formed by the association of one or two of the fusion proteins according to the present invention, wherein the TCR is an alpha/beta-TCR. The inventive T-cell receptor (either comprising a non-modified alpha or beta chain and an inventive fusion protein alpha or beta chain or two modified alpha or beta chains according to the invention) is able to exert its biological function, in particular binding to its specific peptide-MHC complex, and/or a functional signal transduction upon peptide activation.

Another preferred aspect of the present invention relates to a method for producing a fusion protein according to the present invention, comprising a chemical synthesis of said peptide. Methods for chemically synthesizing proteins an peptides are described in the literature, and well known to the person of skill.

Peptides (at least those containing peptide linkages between amino acid residues) may be synthesized by the Fmoc-polyamide mode of solid-phase peptide synthesis as disclosed by Lu et al (1981) J. Org. Chem. 46, 3433-3436, and references therein. Temporary N-amino group protection is afforded by the 9-fluorenylmethyloxycarbonyl (Fmoc) group. Repetitive cleavage of this highly base-labile protecting group is achieved by using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized.

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from Calbiochem-Novabiochem (UK) Ltd, Nottingham NG7 2QJ, UK.

Purification may be effected by any one, or a combination of, techniques such as size exclusion chromatography, ion-exchange chromatography and (usually) reverse-phase high performance liquid chromatography.

Analysis of peptides may be carried out using thin layer chromatography, reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

Another preferred aspect of the present invention then relates to a method for producing a fusion protein according to the present invention, comprising: expressing a nucleic acid molecule encoding a fusion protein according to the present invention in a host cell according to according to the present invention, and purifying said fusion protein or said TCR from said host cell.

One skilled in the art will understand that there are myriad ways to express a recombinant protein such that it can subsequently be purified. In general, an expression vector carrying the nucleic acid sequence that encodes the desired fusion protein will be transformed into a microorganism for expression. Such microorganisms can be prokaryotic (bacteria) or eukaryotic (e.g., yeast). One appropriate species of bacteria is *Escherichia coli* (*E. coli*), which has been used extensively as a laboratory experimental expression system. A eukaryotic expression system will be preferred where the protein of interest requires eukaryote-specific post-translational modifications such as glycosylation. Also, protein can be expressed using a viral (e.g., vaccinia) based expression system.

Protein can also be expressed in animal cell tissue culture, and such a system will be appropriate where animal-specific protein modifications are desirable or required in the recombinant protein. Such expression is particularly appropriate where native assembly and export of the inventive fusion protein is desirable, since the activity of TCRs is influenced by native dimerization (folding and assembly) and presentation on the cell.

The expression vector can include a sequence encoding a targeting peptide positioned in such a way as to be fused to the coding sequence of the functionalized fusion protein. Targeting peptides/domains included in the fusion can be in addition to another functionalizing peptide (such as a tag). Targeting domains may allow the fusion protein to be targeted to specific cellular locations, and may be removed during or soon after synthesis of the fusion protein. In addition, multiple targeting peptides can be included in a single fusion, for instance a peptide/domain that directs the fusion protein if to be secreted, and another peptide/domain that directs the secreted protein to a target (surface of the cell). Various appropriate prokaryotic and eukaryotic targeting peptides, and nucleic acid molecules encoding such, are known to one of ordinary skill in the art. Through the use of a eukaryotic secretion-type signal sequence, the functionalized fusion protein can be expressed in a transgenic animal (for instance a cow, pig, or sheep) in such a manner that the fusion protein is secreted into the milk of the animal. Targeting protein portions also may be used to ensure that a transgenically expressed fusion protein is secreted into the circulatory system of the transgenic animal, thereby permitting the fusion protein to be transported to a target (cell, tissue, organ, etc.).

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter is preferred. This permits selective production of the recombinant protein, and allows both higher levels of production than constitutive promoters, and enables the production of recombinant proteins that may be toxic to the expressing cell if expressed constitutively.

In the context of the present invention, a "peptide" shall refer to any compound containing two or more amino-acid residues joined by amide bonds, formed from the carboxyl group of one residue and the amino group of the next. The broad term "peptide" includes oligopeptides, polypeptides, and proteins.

In the context of the present invention, a "fusion protein" shall mean a protein comprising two amino acid sequences that are not found joined together in nature.

In the context of the present invention, a "peptide tag" shall refer to a peptide sequence that is attached (for instance through genetic engineering) to another peptide or a protein, to provide a function to the resultant fusion. Peptide tags are usually relatively short in comparison to a protein to which they are fused; by way of example, peptide tags are four or more amino acids in length, such as, 5, 6, 7, 8, 9, 10, 15, 20, or 25 or more amino acids. Usually a peptide tag will be no more than about 100 amino acids in length, and may be no more than about 75, no more than about 50, no more than about 40, or no more than about 30.

Another aspect of the present invention then relates to an isolated nucleic acid molecule encoding the fusion protein according to the present invention or the TCR according to according to the present invention. Preferred is a nucleic acid molecule according to the present invention, wherein said molecule is selected from DNA, RNA, PNA, CNA, mRNA or mixtures thereof.

In the context of the present invention, a "peptide nucleic acid (PNA) shall refer to a n oligonucleotide analog with a backbone comprised of monomers coupled by amide (peptide) bonds, such as amino acid monomers joined by peptide bonds.

In the context of the present invention, a "nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Another aspect of the present invention then relates to a vector, preferably in the form of a plasmid, shuttle vector, phagemide, cosmid, expression vector, retroviral vector, retroviral expression vector, adenoviral vector or particle and/or vector to be used in gene therapy, comprising a nucleic acid molecule according to the present invention. Preferably, said vector is used to infect a host cell according to the present invention as described hereinbelow.

In the context of the present invention, a "vector" shall mean a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

In the context of the present invention, "operably linked nucleic acid" shall mean a first nucleic acid sequence that is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

In the context of the present invention, a "recombinant nucleotide" shall mean a recombinant nucleic acid molecule that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

A "transformed" cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Another preferred aspect of the present invention relates to a pharmaceutical composition, comprising a fusion protein according to the present invention, a nucleic acid molecule according to the present invention, a vector according to the present invention or a host cell according to the present invention, together with a pharmaceutically acceptable carrier. Preferred is a medicament containing expanded T-cell host cells for adoptive transfer. Said T-cells can be derived from cells of the patient and/or cells of a donor.

Another preferred aspect of the present invention relates to the use of a pharmaceutical composition according to the present invention for the production of a medicament for the treatment of tumorous and/or infective diseases. Examples are viral infection, such as HIV infection, and cancer, such as renal cancer.

In the context of the present invention, "pharmaceutically acceptable carriers" are the pharmaceutically acceptable carriers useful in the disclosed compositions and methods which are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. Conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. The composition can include carriers that are suitable for lyophilization.

An injectable composition is a pharmaceutically acceptable fluid composition comprising at least one active ingredient, e.g., an expanded T-cell population (preferably autologous to the patient to be treated) expressing a TCR comprising one or more fusion proteins of the invention. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell, as well as chemically synthesized biopolymers.

The term "purified" does not require absolute purity; rather, it is intended as a relative term. Thus, for example, a "purified" fusion protein preparation is one in which the fusion protein is more enriched than the protein is in its generative environment, for instance within a cell or in a biochemical reaction chamber. Preferably, a preparation of fusion protein is purified such that the fusion protein represents at least 50% of the total protein content of the preparation.

Another preferred aspect of the present invention relates to a host cell that is transfected with a vector or infected or transduced with a particle according to the present invention. Preferably, the host cell according to the present invention is a T-cell or a T-cell-precursor cell or a non-pluripotent stem cell, more preferably expressing a fusion protein according to the present invention, in particular a TCR according to the invention, on its surface.

Host cells of the present invention can also be used for screening purposes in order to identify substances that interact with the activity of the fusion protein of the present invention (that is, either the biological function(s) of the protein as such and/or the binding to the epitope-tag of said fusion protein). Methods for screening are well known in the literature and the person of skill will be readily available to adopt these methods in accordance with the present invention. In general, assays to determine a binding and biological effect of a ligand to a specific target (in this case the fusion protein) are well known to the person skilled in the art and can be found, for example, in U.S. Pat. Nos. 4,980,281, 5,266,464 and 5,688,655 to Housey for phenotypic changes of cells after incubation with a screening ligand. Furthermore, U.S. Pat. No. 5,925,333 to Krieger at al. describes methods for modulation of lipid uptake and related screening methods.

The object of the present invention is further solved by a method of treatment of a tumorous or infective disease, comprising a) administering an effective amount of a pharmaceutical composition according to the present invention containing host cells according to the present invention to a patient to be treated, and b) inactivating said host cells by administering an effective amount of an antibody that immunologically recognizes the epitope-tag.

In this aspect of the present invention, a pharmaceutical composition according to the present invention is administered to a diseased patient having a tumorous, autoimmune or infective disease, such as, for example, a viral infection, such as a HIV infection or cancer, such as, for example, renal cancer. In general, all diseases and/or conditions can be treated that involve surface expressed proteins. Preferred is the treatment of diseases that are related to foreign antigens presented on their target cells via MHC class I molecules. Most preferred is a treatment of a disease that can be treated by adoptive transfer methods. Further preferred is a combinatorial treatment, for example one that augments dendritic cell-mediated tumor antigen presentation and antagonize negative immune regulation (Hodi F S, Dranoff G, Combinatorial cancer immunotherapy. Adv Immunol. 2006; 90:341-68). Nevertheless, other combinatorial treatments, in particular in the context of cancer treatments, are known and useful.

Preferably, the treatment is by providing a pharmaceutical composition containing an in vitro expanded autologic recombinant cytotoxic T-cell population that expresses a TCR according to the present invention. Methods for expanding clonal T-cell populations are described in the literature (for example for regulatory T-cells in Karakhanova S, Munder M, Schneider M, Bonyhadi M, Ho A D, Goerner M. Highly efficient expansion of human CD4+CD25+ regulatory T cells for cellular immunotherapy in patients with graft-versus-host disease. J. Immunother. 2006 May-June; 29(3):336-49).

Since the majority of tumor-associated antigens that have been identified in human are self-antigens that are over-expressed in tumors but also occur in normal tissues, the problem exists that adoptively transferred T cells could cause autoimmunity. Furthermore, autoimmunity might result in the modification of ignorant self-specific T cells by TCR gene transfer in a way that these T cells might become auto-aggressive after triggering through their transduced exogenous TCR. For these reason redirected T cells obtained by TCR gene transfer have to be eradicated and/or inactivated, if this is necessary. Inactivation of said cells is usually and preferably performed by binding of the tag to an antibody or fragment thereof, and subsequent inactivation, preferably killing and/or eradication, of the bound cell by cellular mechanisms. It is also possible to couple said antibody or fragment thereof to a cytotoxic moiety, such as a toxin or other cytotoxic substance, in order to kill cells to which the antibody or fragment thereof is bound. Respective techniques and antibody-constructs are also known to the person of skill.

Another preferred embodiment of the method of treatment of a tumorous or infective disease according to the present invention comprises a) providing a host cell population expressing a fusion protein according to the present invention or a TCR according to the present invention on the surface of said host cell in said population, b) enriching said host cell population by performing a method according to the present invention as above, c) formulating said enriched host cell population of b) into a pharmaceutical composition, and d) administering an effective amount of said pharmaceutical composition of c) to a patient to be treated.

In this aspect of the present invention, a host cell population is administered to a patient to be treated having a disease or condition as above, wherein first the host cell population expressing a fusion protein according to the present invention or a TCR according to the present invention is enriched for fusion protein-expressing cells, using the epitope-tag. Then, the enriched host cell population is administered to said patient.

An effective amount of a protein (such as a fusion protein of the disclosure) or a host cell may be administered in a single dose, or in several doses, for example daily, during a course of treatment. However, the effective amount of protein or host cell preparation will be dependent on the protein or cell line applied, the subject being treated, the severity and type of the affliction, and the manner of administration of the protein. For example, a therapeutically effective amount of a fusion protein can vary from about 0.01 mg/kg body weight to about 1 g/kg body weight. In host cell preparations, a predefined number of viable cells will be administered.

The fusion proteins disclosed herein have equal application in medical and veterinary settings. Therefore, the general term "patient being treated" is understood to include all animals (e.g. humans, apes, dogs, cats, horses, and cows).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the compositions and methods herein, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The foregoing and other features and advantages will become more apparent from the following detailed description of the non-limiting example, which proceeds with reference to the accompanying sequences and figures.

[100%–% cytotoxicity (complement alone)]×100. Results show data from one of at least two independent experiments with comparable results. (b) Splenocytes of B6 mice were transduced with either OT-I/TCRwt or OT-I/TCRmyc. 5×10$^6$ TCR-transduced cells were adoptively transferred i.v. into Rag-1$^{-/-}$ recipients. After 13 days blood was stained for CD8-positive and myc-positive cells. One group of mice received 500 µg of a myc-specific antibody (clone 9E10) i.p. for depletion. One day after antibody injection blood samples were collected and stained with CD8- and myc-specific antibodies for the TCRmyc construct or with CD8-, vα2- and vβ5-specific antibodies for the TCRwt construct, respectively. Stainings show cells gated on CD8-expression and represent one of two treated animals.

Figure 8:
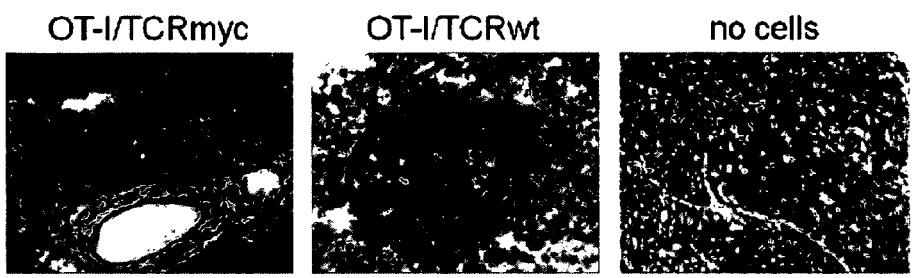
Figure 8:
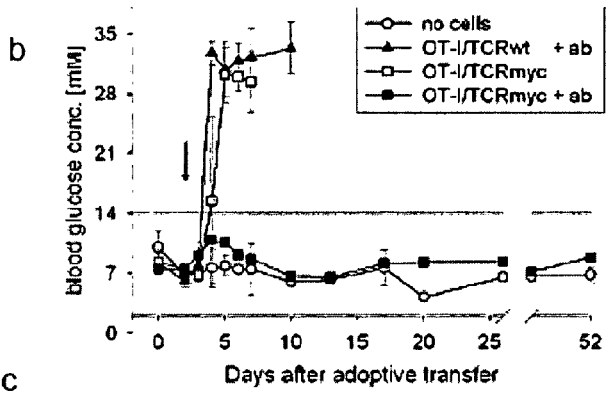
Figure 8:
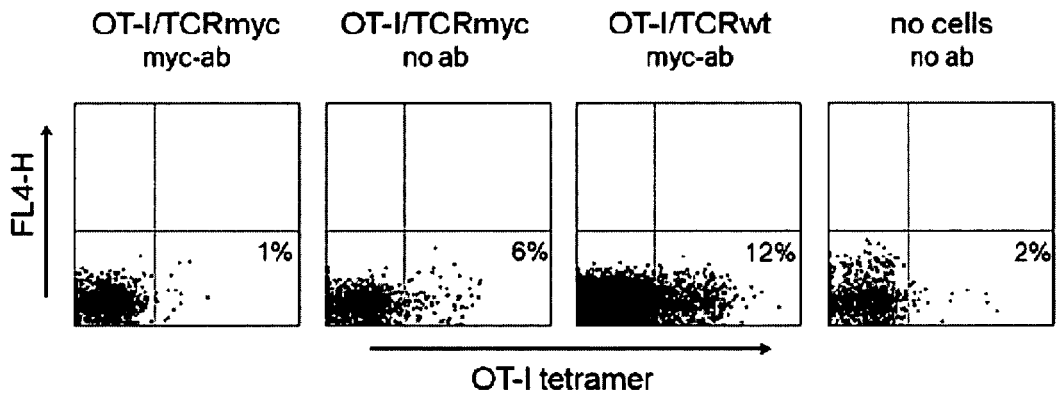
Figure 8:
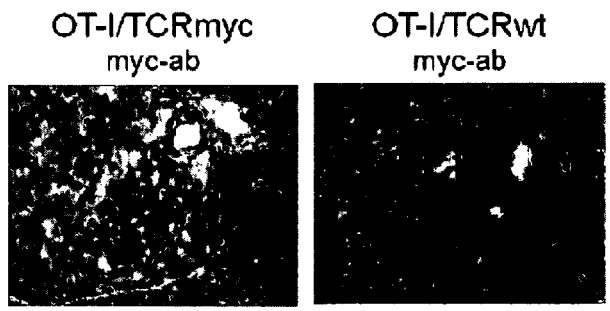

FIG. 8 shows the prevention of auto-immune diabetic disease mediated by myc-specific antibody depletion. B6 splenocytes were transduced with either OT-I/TCRwt or OT-I/TCRmyc and 2×10$^7$ TCR-positive cells were injected i.v. into sublethally irradiated RIP-mOVA mice. Mice which were irradiated but received no cells served as a negative control. (a) Two days after adoptive transfer pancrei of mice from each group were frozen and analyzed by immunohistochemistry with a CD8-specific antibody. (b) 500 µg of a myc-specific antibody was administered i.p. into all mice which had received T cells harboring the TCRwt (n=5) and half of the mice (n=5) which had received T cells carrying the TCRmyc (arrow). A control group (n=5) which had received OT-I/TCRmyc-transduced cells was not treated with antibody. Blood glucose concentration was determined. Depicted are mean values of all animals in one group; error bars indicate the standard deviation. If measurement exceeded the upper detection limit of 33.3 mM, values were set as 35 mM to allow the calculation of mean blood glucose levels. (c) Lymphocytes were isolated from mesenterial lymph nodes of animals from all groups and analyzed with a CD8-specific antibody and OT-I specific tetramer in flow cytometry. Depicted cells are gated on positive CD8 expression. (d) Pancrei from diabetic and control mice were frozen and analyzed with a CD8-specific antibody in immunohistochemistry.

Figure 9:
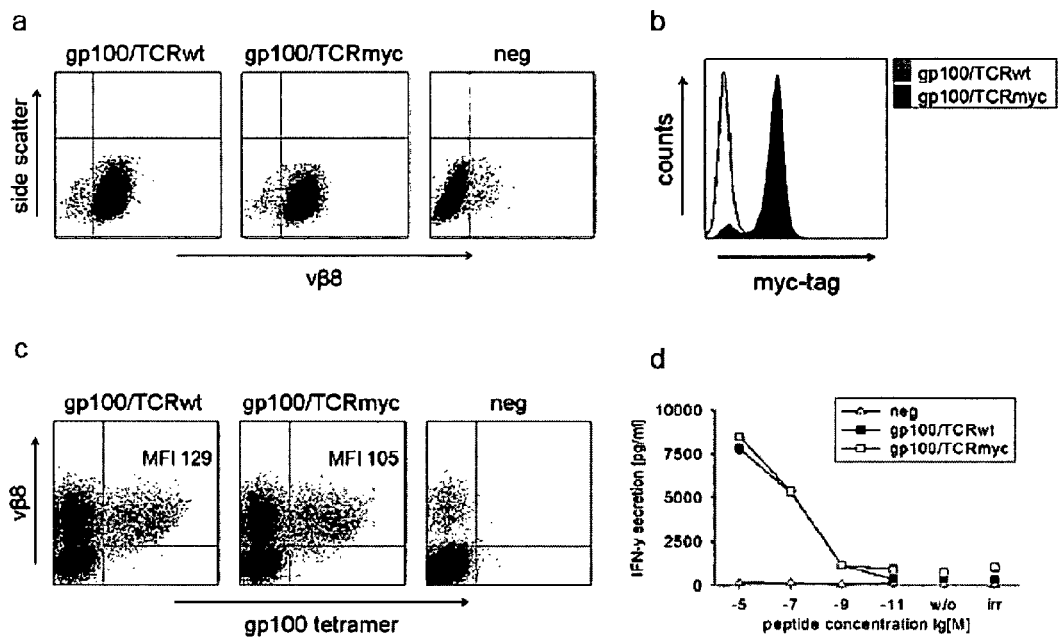

FIG. 9 shows that the human gp100/TCRmyc is expressed and functions comparable to gp100/TCRwt. (a) The human T cell line HuT 78 was transduced with gp100/TCRwt or gp100/TCRmyc and enriched with β-chain specific antibodies. TCR expression was analyzed by flow cytometry staining with a vβ8-specific antibody. Untransduced cells (neg) served as a negative control. (b) HuT 78 cells transduced with gp100/TCRmyc were stained with a myc specific antibody and analyzed by flow cytometry. Cells transduced with the unmodified wildtype receptor served as a negative control. (c) PBLs were transduced with gp100/TCRwt or gp100/TCRmyc vectors and stained with a vβ8-specific antibody and a gp100-specific tetramer. Untransduced PBLs (neg) show the background of endogenous vβ8-positive T cells. Numbers indicate the mean fluorescence intensity (MFI) of the tetramer staining. (d) gp100/TCRwt- or gp100/TCRmyc-transduced PBLs were co-cultured with T2 cells pulsed with 10 µM to 10 pM gp100-peptide for 24 hours. Untransduced PBLs were used as a negative control (neg). Culture supernatant was analyzed for IFN-γ content by ELISA. Unloaded T2 cells (w/o) or T2 cells loaded with irrelevant peptide (irr) served as a negative target control. Data represent mean values of duplicates and error bars indicate standard deviation. At least two independent experiments with two different donors each were performed with reproducible results.

Figure 10:
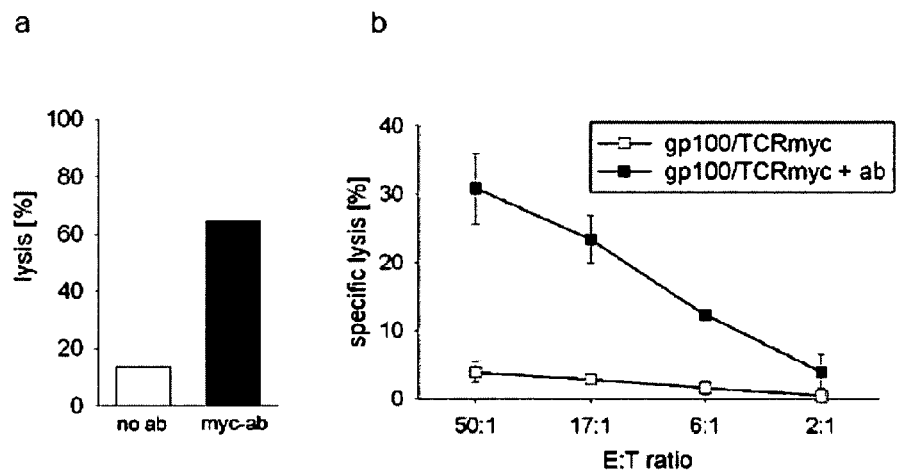

FIG. 10 shows that T cells transduced with gp100/TCRmyc can be depleted in vitro by complement and cell-mediated lysis. PBLs were transduced with gp100/TCRmyc retroviruses, sorted for myc-expressing cells and restimulated with gp100-peptide pulsed T2 cells. (a) For complement-mediated depletion cells were incubated for one hour with a myc-specific antibody (clone 3A7) and subsequently with rabbit complement factors for two hours. 7-AAD was used to discriminate between living and dead cells. Cells incubated without antibody served as a negative control. (b) Autologous PBMCs enriched for NK cells served as effector cells. $^{51}$Chromium-labeled myc-positive PBLs were incubated with effector cells in effector to target ratios from 50:1 to 2:1. A myc-specific antibody (clone 9E10) and a secondary rabbit anti-mouse IgG1 antibody were added. Lysis was measured in a standard four-hour chromium release assay. Samples without antibody served as a negative control. Data represent mean values of duplicates and error bars indicate the standard deviation. The results were reproduced in two independent experiments with two different donors.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand. In the accompanying sequence listing:
SEQ ID NOs: 1 and 2 show the amino acid sequences of the myc-TCR constructs "doubleloop" (SEQ ID No. 1), having two tandem-tags in the loop-region of the beta-chain, and "double alpha N-term" (SEQ ID No. 2), having two tandem tags at the N-terminus of the alpha-chain.

EXAMPLES

In one preferred aspect thereof, the present invention is directed to establishing a new safety mechanism to eliminate genetically modified cells (e.g. T cells) used in, for example, adoptive cell transfer. For this, T cell receptor molecules are modified by introducing a short nucleotide sequence encoding a part of the myc gene (myc-tag) to be transferred into cells. When the myc-tagged cells will be used in adoptive transfer, they should be able to exert normal cytotoxic function. If it becomes necessary, the therapy can be terminated by administering a myc-specific antibody to the patient which should bind to the tag on the surface of the transferred cells and lead to depletion or neutralization of the cells.

In order to prove the general applicability of the concept of the present invention, the myc-tag was integrated into the mouse-TCR "P14" at nine different positions. Two of these myc-TCR constructs, namely the construct "doubleloop" (SEQ ID No. 1), having two tandem-tags in the loop-region of the beta-chain, and "double alpha N-term" (SEQ ID No. 2), having two tandem tags at the N-terminus of the alpha-chain could be depleted in vitro by incubation with a myc-specific antibody and rabbit-complement factors, but not by antibodies or complement alone (as expected). The depletion could be shown in two different T-cell lines, and also in primary mouse-T-cells. Die modified TCRs were as functional as the non-modified wildtype-TCR, as could be shown in an indicator cell line. In addition, the identical positions were modified in a human TCR using the myc-tag and also these TCRs remained functional.
Methods
Mice
C57BL/6J mice were purchased from Charles River (Sulzfeld, Germany). Rag-1$^{-/-}$(B6.129S7-Rag1$^{tm1Mom}$) were obtained from The Jackson Laboratory (Bar Harbor, USA). RIP-mOVA mice (a gift from M. Canarille, Munich, Germany) express chicken ovalbumin under control of the rat insulin promoter in the β islet cells of the pancreas. All mice were housed and bred under institutional guidelines. Animal experiments were approved by the responsible institution and performed according to national and regional regulations.

Molecular Cloning of myc-Tagged TCRs and Retroviral Constructs

The OT-I TCR (vα2/vβ5, recognizing the chicken ovalbumin$_{257-264}$ peptide fragment SIINFEKL (SEQ ID NO: 4) was isolated from cDNA of splenocytes of OT-I/Rag-1−/− mice (Schuler, T. & Blankenstein, T. Cutting edge: CD8+ effector T cells reject tumors by direct antigen recognition but indirect action on host cells. *J Immunol* 170, 4427-4431(2003)) and cloned into the MP71 retroviral vector (Engels, B. et al. Retroviral vectors for high-level transgene expression in T lymphocytes. *Hum Gene Ther* 14, 1155-1168 (2003)) via NotI and BsrGI restriction sites. Construction of P14 TCR (vα2/vβ8, recognizing the lymphocytic choriomeningitis virus (LCMV) glycoprotein$_{33-41}$ peptide KAVYNFATM (SEQ ID NO: 5)) and gp100 TCR (vα13/vβ8, recognizing human gp100$_{29-217}$ IMDQVPFSV (SEQ ID NO: 6)) vectors have been described (Sommermeyer, D. et al. Designer T cells by T cell receptor replacement. *Eur J Immunol* 36, 3052-3059 (2006), Morgan, R. A. et al. High efficiency TCR gene transfer into primary human lymphocytes affords avid recognition of melanoma tumor antigen glycoprotein 100 and does not alter the recognition of autologous melanoma antigens. *J Immunol* 171, 3287-3295 (2003)). In bicistronic constructs the α- and the β-chain were linked via the P2A peptide (Arnold, P. Y., Burton, A. R. & Vignali, D. A. Diabetes incidence is unaltered in glutamate decarboxylase 65-specific TCR retrogenic nonobese diabetic mice: generation by retroviral mediated stem cell gene transfer. *J Immunol* 173, 3103-3111 (2004)) to obtain MP71-TCRα-P2A-TCRβ.

Only generation of the construct carrying two myc-tags at the N-terminus of the OT-I TCRα-chain is described. Insertion of the first myc-tag (amino acid sequence EQKLISEEDL SEQ ID NO: 7) into the TCRα-chain was facilitated with pairs of overlapping primers. First, the signal peptide was amplified using a 5'-primer (P1) with a NotI restriction site and a 3'-primer encoding the myc-tag sequence (P2). The variable and constant regions of the α-chain were amplified using a 5'-primer containing the myc-tag sequence (P3) and a 3'-primer with a BsrGI restriction site (P4). Second, the fragments were combined in a separate PCR reaction using the primers P1 and P4 and cloned into the MP71 vector. The second myc-tag was inserted by annealing the oligos M1 and M2 to a doublestranded fragment which was subsequently cloned into the TCRmyc via the BclI restriction site.

Cell Culture and Production of TCR Retroviruses

T2, T2-K$^b$ (a gift from H. Schreiber, Chicago, USA), RPMI 8866 cells (kindly provided by G. Trinchieri, Philadelphia, USA), HuT 78 (ATCC TIB-161, American Type Culture Collection, Manassas, USA)) and 58 cells (Letourneur, F. & Malissen, B. Derivation of a T cell hybridoma variant deprived of functional T cell receptor alpha and beta chain transcripts reveals a nonfunctional alphamRNA of BW5147 origin. *Eur J Immunol* 19, 2269-2274 (1989)) were grown in RPMI1640 medium (Invitrogen, Karlsruhe, Germany) supplemented with 10% fetal calf serum (FCS, Biochrom, Berlin, Germany), 10 mM HEPES and 100 U/ml penicillin/streptomycin (T cell medium). 293T cells (ATCC CRL12 11268) and the ecotropic packaging cell line Plat-E (Morita, S., Kojima, T. & Kitamura, T. Plat-E: an efficient and stable system for transient packaging of retroviruses. *Gene Ther* 7, 1063-1066 (2000)) were cultured in DMEM medium (Invitrogen) with 10% FCS and 100 U/ml penicillin/streptomycin.

Murine splenocytes were isolated from eight to ten week old mice and prepared as a single cell suspension. Red blood cells were lysed using NH$_4$Cl treatment. Murine T cells were stimulated with 1 μg/ml CD3-specific antibody and 0.1 μg/ml CD28-specific antibody (both Pharmingen, Hamburg, Germany) for two days and cultured in RPMI1640 medium supplemented with 10% FCS, 1 mM HEPES, 100 U/ml penicillin/streptomycin, 1 mM sodium pyrovate, 50 μM 2-mercaptoethanol and 40 U/ml recombinant IL-2 (Proleukin, Chiron, Marburg, Deutschland). Human peripheral blood mononuclear cells (PBMCs) were isolated from healthy donors after informed consent by centrifugation on Ficoll-Hypaque and grown in T cell medium with 400 U/ml Proleukin. PBMCs were stimulated for two days with immobilized CD3-specific (5 μg/ml) (CILAG, Sulzbach, Germany) and CD28-specific antibodies (1 μg/ml) (Pharmingen).

To produce ecotropic TCR retrovirus for transduction of murine T cells, Plat-E cells were transiently transfected with the vector construct using calcium phosphate precipitation. Amphotropic virus supernatant for the transduction of human T cells was produced by triple transfection of 293 T cells with the vector construct, pcDNA3.1MLVg/p (C. Baum, Hannover, Germany) encoding murine leukemia virus (MLV) gag and pol genes and pALF-10A 1GaV46 encoding MLV 10A1 env gene. 48-hour culture supernatant of the packaging cells was harvested and filtered through 0.45 μm pore size filters.

Transduction of T Cells

T cell lines (1×10$^5$ cells per well) and primary human T cells (1×10$^6$ per well) were transduced in 24-well non-tissue culture plates coated with RetroNectin (TaKaRa Bio, Otsu, Japan) as described (Engels, B. et al. Retroviral vectors for high-level transgene expression in T lymphocytes. Hum Gene Ther 14, 1155-1168 (2003)). Murine splenocytes were transduced in 6-well non-tissue culture plates (6×10$^6$ per well) in the same way.

Peptides, Antibodies and Multimers

Ova-peptide (SIINFEKL (SEQ ID NO: 4)), gp33-peptide (KAVYNFATM SEQ ID NO: 5)) and gp100-peptide (IMDQVPFSV SEQ ID NO: 6)) were purchased as HPLC-purified products (Biosyntan, Berlin, Germany). FITC-, PE- or allophycocyanin-labeled monoclonal antibodies (mAbs) directed against murine vα2, vβ5, vβ8, CD3 and CD8 were obtained from BD (Heidelberg, Germany). Human vβ8-specific antibody was purchased from Immunotech (Marseille, France). PE- or allophycocyaninlabeled tetramers were used to stain gp100 TCR (Immunomics, Fullerton, USA), P14 TCR (Immunotech) and OT-I TCR (Dirk Busch, LMU Munich, Germany). Fluorescence intensity was measured using a FACSCalibur flow cytometer and CellQuestPro software (BD). Data analysis was performed with FlowJo software (Tree Star, Ashland, USA). The myc-specific antibody 3A7 of IgG2a subtype used for complement lyses experiments was obtained from US Biologicals (Swampscott, USA). The IgG1 subtype myc-specific antibody clone 9E10 which was used for staining, in vivo depletion and ADCC assays was purified from hybridoma supernatant (ATCC CRL-1729).

Cytokine Release Assay

Peptide-presenting target cells were incubated for two hours at 37° C. with different amounts of peptide in serum-free medium and washed twice. Per well 1×10$^5$ effector cells were cocultured with peptide-loaded targets in a 1:1 ratio in 96-well round-bottom plates (Corning Costar, Munich, Germany) for 24 hours at 37° C. The supernatant was tested for human IFN-γ or murine IL-2 content by enzyme-linked immunosorbent assay (ELISA) (sensitivity 4 or 2 pg/ml, respectively; eBioscience, San Diego, USA).

Complement-Mediated Depletion Assay

Exponentially growing 58 cells or Ficoll-Hypaque purified PBLs were seeded in a 96-well plate (Corning Costar) with 1×10$^5$ cells/well in RPMI1640 medium plus 25 mM HEPES and 0.3% BSA. Cells were labeled with 1 μg myc-specific antibody/well (clone 3A7) for one hour at 4° C., washed and incubated with rabbit complement (for 58 cells: LOW-TOX-M; for PBLs: Rabbit Complement MA, both Cedarlane, Hornby, Canada) at 1:6 or 1:9 dilution for two hours at 37° C. For live and dead cell discrimination cells were stained with 7-AAD (BD Biosciences) for ten minutes and analyzed by flow cytometry. Cells incubated with antibody or complement alone served as controls. Percent of specific depletion was calculated as [% cytotoxicity (antibody+complement)−% cytotoxicity (complement alone)]/[100%−cytotoxicity (complement alone)]×100.

Antibody-Dependent Cell-Mediated Cytotoxicity Assay (ADCC)

Target cells were prepared by enriching TCR-transduced PBLs using myc-specific magnetic beads and MACS separator columns (Miltenyi Biotec, Bergisch Gladbach, Germany) and specifically restimulating them with irradiated peptide-loaded T2 cells. Autologous PBMCs enriched for natural killer (NK) cells served as effector cells. For NK enrichment freshly isolated PBMC were centrifuged on Ficoll-Hypaque, depleted of monocytes by adhesion to cell culture plastics and stimulated for 6 days with RPMI 8866 cells irradiated with 64 Gy. For stimulation 300 U/ml Proleukin were added to the effector cells one day prior to the ADCC assay. After stimulation, about 50% of the effector cells displayed an NK phenotype (CD3-negative, CD56-positive). Lysis was performed by incubating 5×10$^3$ $^{51}$Cr-labeled (Amersham, Buckinghamshire, UK) target cells (100 μCi per sample) with effector cells in effector-to target ratios from 50:1 to 2:1 for four hours in the presence of 1 μg myc-specific antibody (clone 9E10) and 1 μg rabbit anti-mouse IgG1-Fc polyclonal antibody (Jackson ImmunoResearch, West Grove, USA).

Adoptive T Cell Transfer

RIP-mOVA mice were sublethally irradiated with 400 rad one day before adoptive transfer. Age- and sex-matched recipient mice were injected i.v. in the tail vein with 2×10$^7$ (RIP-mOVA mice) or 5×10$^6$ (Rag-1$^{-/-}$ mice) TCR-positive splenocytes one day after the second transduction. For depletion of adoptively transferred cells, 500 μg myc-specific antibody (clone 9E10) were injected i.p. two (RIP-mOVA) or 13 (Rag-1$^{-/-}$) days after adoptive transfer. Expansion and depletion of cells was monitored by flow cytometry of blood samples. Diabetes development in RIP-mOVA mice was followed by measuring blood glucose levels with Ascensia ELITE SENSOR strips (Bayer, Leverkusen, Germany). Mice with blood glucose levels higher than 14 mM at two consecutive days are considered diabetic.

Immunohistochemical Staining

Pancrei of sacrificed mice were embedded in Tissue Tek (Sakura Finetek, Zoeterwoude, Netherlands) and frozen in liquid nitrogen. Microsections of the organs were prepared and mounted on microscope slides. Slides were preincubated in 5% rat serum and subsequently stained with biotin-conjugated CD8-specific antibody (Caltag, Karlsruhe, Germany) and streptavidin-alkaline phosphatase (Roche, Mannheim, Germany). After adding substrate (Fast Red Substrate System, DAKO, Carpinteria, USA) cells were counter-stained with Mayer's hematoxylin (DAKO).

Example 1

The murine TCR P14 which recognizes an antigenic peptide on the LCMV gp33 protein has been modified with a myc-tag (EQKLISEEDL SEQ ID NO: 7)) at nine different sites. As a model, the 10 amino acids constituting the myc-tag were inserted into the murine P14 TCR recognizing an epitope of the lymphocytic choreomeningitis virus (LCMV) gp33 protein. In one construct, two myc-tag sequences were attached to the N-terminus of the alpha-chain. In a second, 10 amino acids of a protruding loop region in the beta-chain constant domain were exchanged for the sequence of two myc-tags. The TCR genes were cloned into retroviral vectors which were used to transfect the packaging cell line PlatE. Supernatant of transfected cells was used to transduce the two murine T cell lines 58alpha-beta-cells and B3Z cells. Similarly, a TCR for CC-26 tumor associated antigen has been modified and tested.

Both myc-tag-modified TCRs were expressed at the surface of the two cell lines as shown by staining with antibodies specific for the variable region of the TCR chains. Tetramer staining revealed that both TCRs were able to bind to their specific peptide-MHC complex. Furthermore, cells expressing the modified TCRs showed functional signal transduction upon peptide activation as shown with the indicator cell line B3Z.

Figure 1:
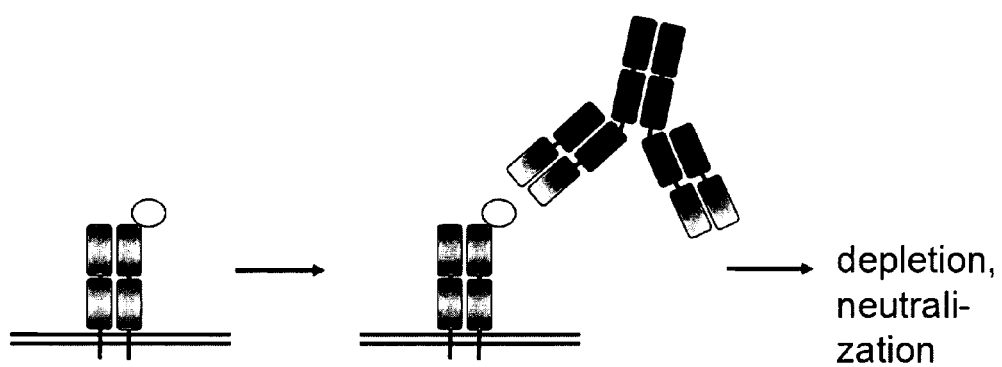
FIG. 1 shows a schematic outline of one embodiment of the general strategy of the epitope-tagged TCR according to the invention.
Figure 2:
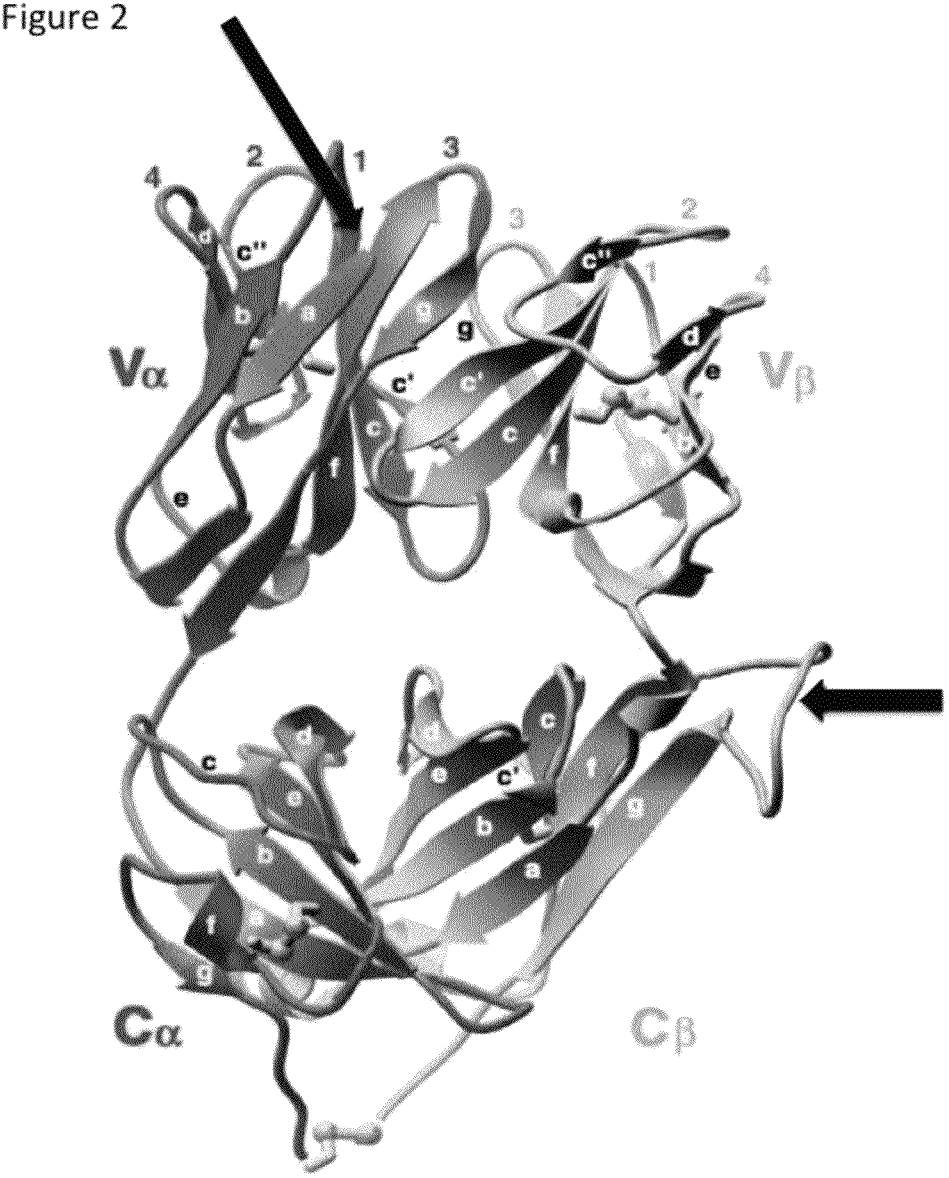
FIG. 2 shows the overview of the mP14 TCR (example 1), for which 9 constructs were made. The mutants that were introduced were designated "loop 1, loop 2, loop 3, the doubleloop (SEQ ID No. 1), the extraloop, alpha-N-term, double alpha N-term (SEQ ID No. 2), beta N-term and c-strand (constant alpha). The positions of the two mutants are indicated by arrows.
Figure 3:
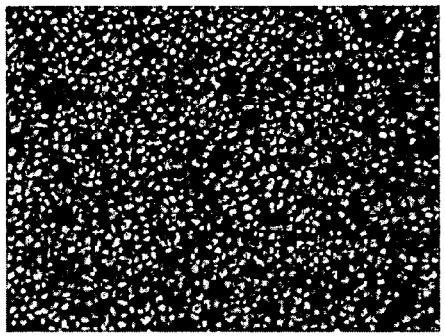
FIG. 3 shows the tests for the functionality of myc-tagged TCRs according to the invention. Column I. is GP33, i.e. specific, and column II. is SIY (negative control). A. negative control, B. P14 wild type, C. P14 double N-term, and D. P14 doubleloop. Dark spots show functionality of the TCR.
Figure 3:
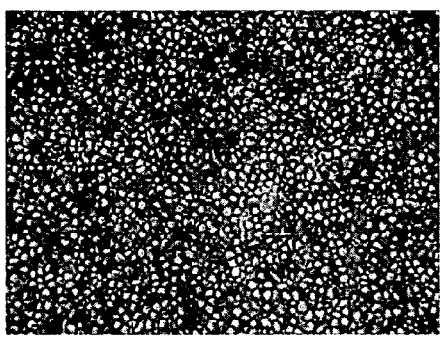
Figure 3:
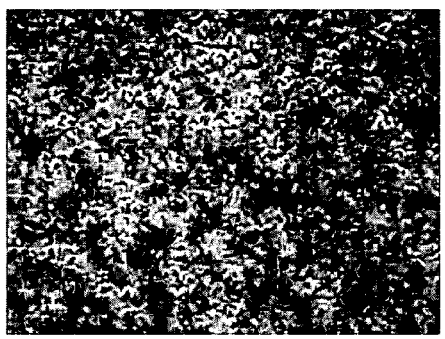
Figure 3:
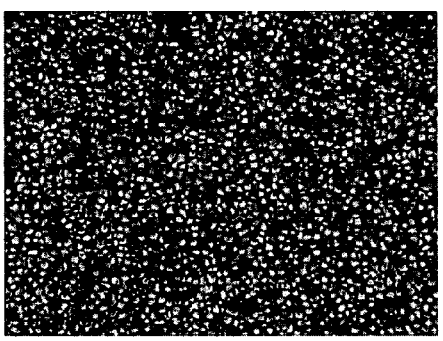
Figure 3:
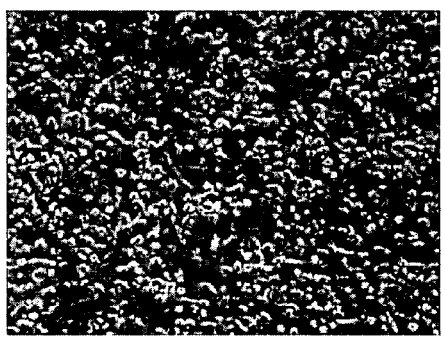
Figure 3:
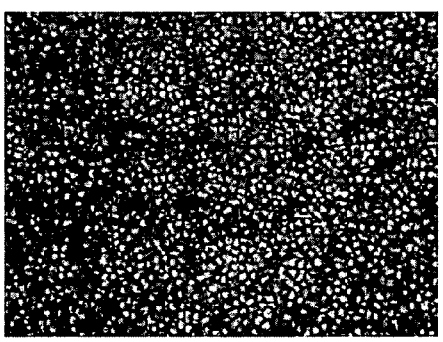
Figure 3:
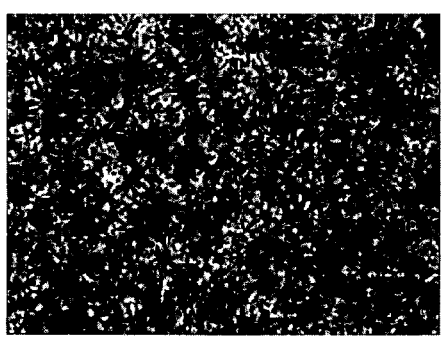
Figure 3:
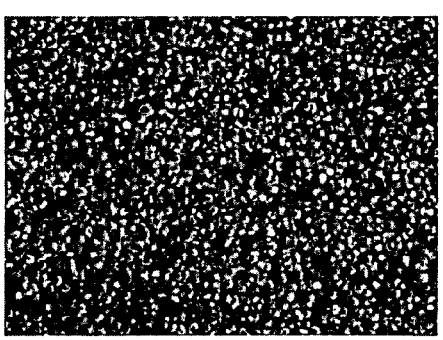
Figure 4:
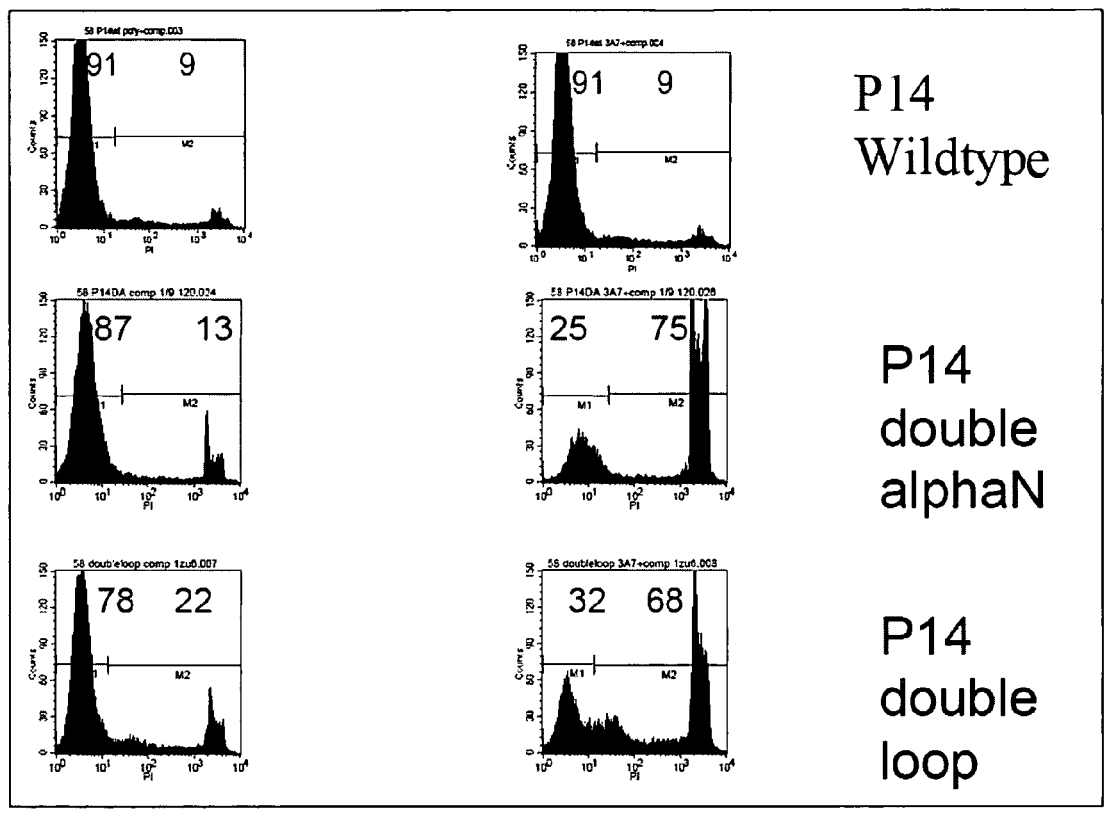
FIG. 4 shows in vitro complement depletion assays. Left column, complement only, right column myc-antibody plus complement. It can be seen that only myc-TCRs are depleted by the addition of antibody plus complement (right column, right peak at P14 tagged-TCRs).
Figure 5:
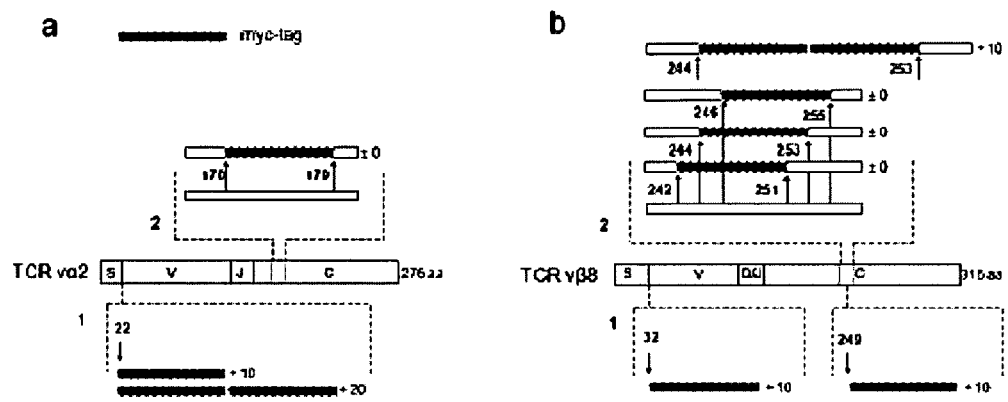
FIG. 5 shows Positions of myc-tag insertion in the murine P14 TCR. The 10 amino acid (aa) myc-tag sequence was incorporated into the sequence of the TCRα-(a) or TCRβ-chain (b). Four constructs were generated, in which one or two myc-tags were inserted at a certain position (1). In this case the length of the protein is extended by +10 or +20 aa. Numbers indicate the aa position in front of which the tag was inserted. In five constructs sequences of the original TCR were substituted with one or two myc-tag sequences (2). Here, numbers indicate the first and last aa position of the original sequence that was replaced. These constructs either do not change in overall number of amino acids if only one tag was inserted (±0), or contain 10 additional aa if two tags replace the original sequence. (S: signal peptide, V: variable region, D: diversity region, J: joining region, C: constant region).

In particular, the inventors sought to introduce the amino acid sequence 409-419 of the human c-myc protein (myc-tag) into the structure of a TCR in a position where it can be recognized by a myc-specific antibody without interfering with TCR function. Based on crystal structures of human and murine TCRs 32, the inventors selected nine different sites in the murine P14 TCR (recognizing an LCMV glycoprotein-derived peptide) α- and β-chain for tag-insertion. The inventors generated retroviral constructs, in which either one or two tags were inserted in a specific position; or parts of the original TCR were substituted by one or two tags (FIG. 5). Interestingly, all constructs were expressed in T cell lines and recognized the antigen as shown by specific tetramer-staining. However, only two constructs that preferably carried a double myc-tag either at the N-terminus of the variable region of the TCRα-chain or in the constant region of the TCRβ-chain allowed in vitro depletion of T cells. Because the depletion of the TCRα-chain modified construct was most efficient, this site was chosen for myc-tag insertion into different TCRs.

Figure 6:
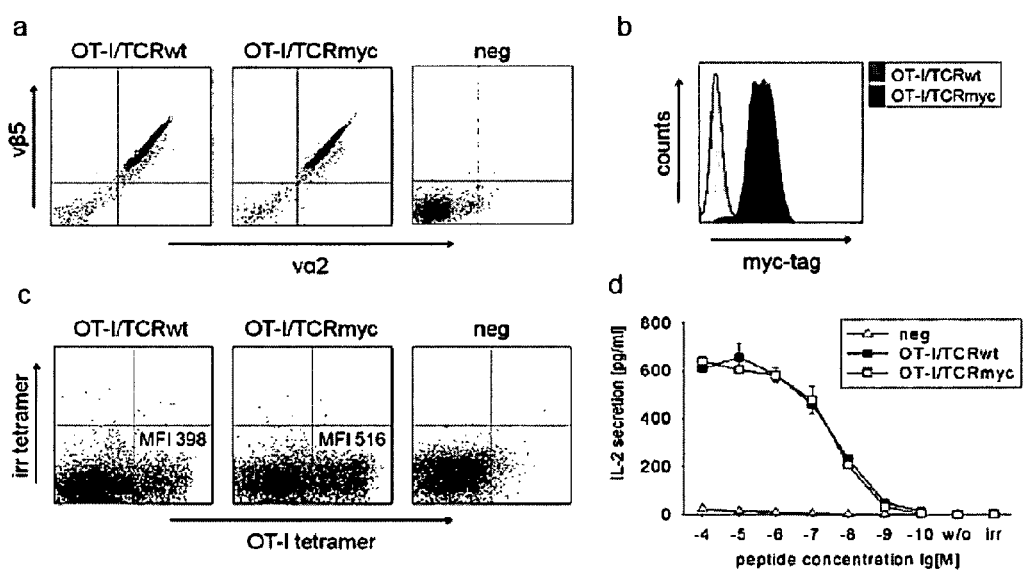
FIG. 6 shows that OT-I/TCRmyc is expressed and functions comparable to TCRwt. (a) TCR-deficient 58 cells were transduced with the indicated OT-I TCR constructs. Cells were enriched with β-chain specific antibodies via FACS sorting and one week later analyzed by flow cytometry with vα2- and vβ8-specific antibodies. Untransduced cells (neg) served as a negative control for TCR expression. (b) 58 cells transduced with the OT-I/TCRmyc were stained with an antibody specific for the myc-tag sequence. Cells transduced with the wild-type receptor were used as a negative control. (c) B6 splenocytes were transduced with either OT-I/TCRwt or OT-I/TCRmyc and after 72 hours stained with a CD8-specific antibody, an OT-I specific MHC-tetramer and an irrelevant tetramer (irr). Depicted cells are gated on CD8 expression. Numbers indicate the mean fluorescence intensity (MFI) of the tetramer staining. (d) $1 \times 10^5$ OT-I/TCRwt- and OT-I/TCR-myc-transduced 58 (CD8α+) cells or untransduced cells (neg) were stimulated for 24 hours with $1 \times 10^5$ T2-Kb cells pulsed with 100 µM to 100 pM of ovapeptide. IL-2 content of the culture supernatant was analyzed by ELISA. Unloaded T2-Kb cells (w/o) or T2-Kb cells loaded with irrelevant peptide (irr) served as a negative control. Data represent mean values of duplicates and error bars indicate the standard deviation.

The inventors generated retroviral constructs encoding the OT-I TCR, which recognizing an ovalbumin-(ova-) derived peptide, either myc-tagged (OT-I/TCRmyc) or wild-type (OT-I/TCRwt). TCRα- and TCRβ-chain encoding retroviruses were used to transduce the TCRαβ-deficient murine T cell line 58. Cells were enriched with an antibody specific for the TCRβ-chain and then analyzed by flow cytometry. TCRα-(vα2) and TCRβ-(vβ5) chain specific antibodies were used to confirm similar expression levels of OT-I/TCRwt and OT-I/TCRmyc (FIG. 6a). Incubation with a myc-specific antibody revealed only binding to OT-I/TCRmyc-modified cells, but not to OT-I/TCRwt-transduced cells (FIG. 6b). Similar results were obtained with the P14 TCR.

T Cells Transduced with myc-Tagged and Wild-Type TCRs Exhibit Comparable Functionality For the clinical application of myc-tagged TCRs it is essential that the receptor function is not impaired by the insertion of the tag. Functional characterization of myc-tagged TCRs was accomplished by staining with peptide-MHC multimers and detection of interleukin (IL)-2 secretion upon specific antigenic stimulus. For this, splenocytes of C57BL/6J (B6) mice were transduced with OT-I/TCRmyc and OT-I/TCRwt retroviruses, respectively and stained with OT-I specific and irrelevant tetramer. Both TCRs similarly bound the ova-antigen as shown by comparable mean fluorescence intensity (MFI) of tetramer staining in flow cytometry (FIG. 6c). For detection of cytokine secretion CD8α-positive 58 cells were transduced with OTI/TCRmyc or OT-I/TCRwt retroviruses with a similar efficiency (93%, data not shown) and stimulated with peptide-loaded T2 cells transfected to express murine MHC-1H-2 Kb molecules. Secretion of IL-2 was detected in a peptide concentration-dependent manner and was similar for cells transduced with both constructs (FIG. 6d). All functional data were reproduced for P14/TCRmyc compared to P14/TCRwt.

T Cells Expressing myc-Tagged TCRs can be Depleted In Vitro and In Vivo

Figure 7:
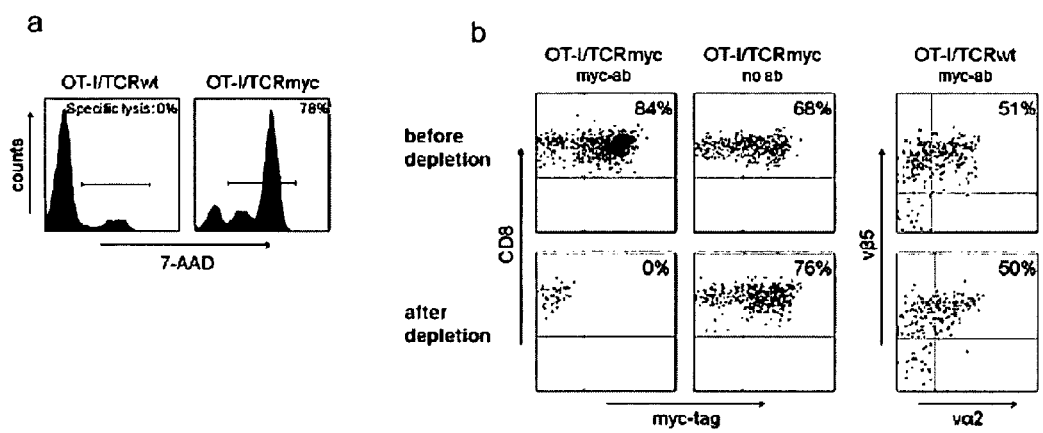
FIG. 7 shows TCRmyc-transduced T cells can be depleted in vitro and in vivo with a myc-specific antibody. (a) TCR-deficient 58 cells were transduced with the OT-I/TCRwt and OT-I/TCRmyc and enriched with β-chain specific antibodies. For depletion cells were incubated for one hour with a myc-specific antibody (clone 3A7) and subsequently with rabbit complement factors for two hours. 7-AAD was used to discriminate between living and dead cells. Numbers indicate specific lysis calculated as [% cytotoxicity (antibody+complement)−% cytotoxicity (complement alone)]/

One pathway of antibodies to induce depletion of target cells is complement factor lysis. To analyze whether TCR-myc-expressing T cells can be depleted with a myc-specific antibody, TCR-enriched 58 cells (>95% purity) were subjected to complement lysis by incubation with a myc-specific antibody and complement factors. Cell viability was determined using 7-amino-actinomycin D (7-AAD) staining. OT-I/TCRmyc-positive cells showed specific lysis of 78%, while OT-I/TCRwt-transduced cells were not lysed. Some unspecific lysis was observed when cells were incubated with complement alone accounting for the small percentage of dead cells in the population transduced with the wild-type TCR (FIG. 7a). The results were reproduced for 58 cells transduced with either P14/TCRmyc or P14/TCRwt with similar results.

To demonstrate that TCRmyc-modified T cells can also be depleted in vivo, splenocytes of B6 mice were transduced with either OT-I/TCRwt or OT-I/TCRmyc retroviruses. One day after transduction, cells were injected into T and B cell-deficient Rag-1$^{-/-}$ mice. Flow cytometry analysis of blood samples taken 13 days after injection demonstrated circulation of the adoptively transferred cells in the blood (FIG. 7b). A myc-specific antibody was injected and blood samples were analyzed one day later. In mice that received OT-I/TCRmyc transduced T cells, no myc-positive cells could be detected, indicating that TCRmyc-transduced cells were completely depleted, whereas in mice that received OT-I/TCRwt T cells or in mice, which did not receive antibody treatment, the population of adoptively transferred cells was virtually unchanged (FIG. 7b).

Depletion of myc-Tagged T Cells Rescues Mice from Lethal Auto-Immune Diabetic Disease After Adoptive Transfer To analyze whether myc-tagged TCRs can be used to prevent auto-immune disease, the inventors used the RIP-mOVA mouse model. These mice express ova under the control of the rat insulin promoter in the β-islet cells of the pancreas. If OT-I/TCR T cells are transferred into these mice, they develop auto-immune diabetes due to destruction of insulin-producing cells by the T cells. Disease progression can be followed by measuring the concentration of blood glucose. Splenocytes from B6 mice were transduced either with OT-I/TCRmyc or OTI/TCRwt retroviruses. Cells were injected one day later into sublethally irradiated RIP-mOVA mice. In this disease model, induction of auto-immune diabetes is extremely rapid with blood glucose values increasing from normal to highly glycaemic within 24 hours at day four to five after adoptive transfer. Due to severity of symptoms mice have to be sacrificed at day six to ten. This fast onset of disease made it necessary to administer the myc-specific antibody for the elimination of transferred cells at day two after adoptive transfer. At this time point the islets of the pancreas of injected mice (but not of untreated animals) were already infiltrated with CD8-positive cells demonstrating onset of disease although no increase of blood glucose level was yet observed (FIG. 8a). None of the animals which received OT-I/TCRmyc T cells and antibody treatment developed diabetes as measured by blood glucose concentration until the end of the observation period on day 52. In contrast, all animals in the control groups (receiving either OT-I/TCRwt T cells plus antibody or OT-I/TCRmyc T cells, but no antibody) succumbed to the disease within four to five days after adoptive T cell transfer (FIG. 8b) and had to be sacrificed two to six days after onset of disease due to severe symptoms (weakness, loss of weight). OT-I tetramer-positive cells were detected in mesenterial lymph nodes of diabetic mice, but not in antibody-treated animals as shown by flow cytometry (FIG. 8c). Immunohistochemical staining of pancreatic sections revealed infiltration of the organ with CD8-positive T cells and lack of pancreatic islet structure in non-depleted animals, but not in antibody-treated mice (FIG. 8d).

Human TCRmyc T Cells are Functional Comparable to TCRwt Cells and can be Depleted In Vitro To assess whether the myc-tag can also be applied as a safeguard to eliminate human TCR redirected T cells, the inventors modified a human TCR which is reactive against the melanoma antigen gp100 with two myc-tags at the N-terminus of the α-chain—corresponding to the same position modified in the murine TCRs. Retroviral constructs were generated and used to transduce the human T cell line HuT 78. The cells were enriched with β-chain specific antibodies. Both, the modified and the wild-type TCR showed similar expression levels when cells were stained with a vβ8-specific antibody (FIG. 9a). Because no antibodies are available for the detection of the gp100α-chain, this staining could not be performed. T cells transduced with the gp100/TCRmyc, but not cells transduced with gp100/TCRwt were detected with a myc-specific antibody by flow cytometry (FIG. 9b). For functional comparison, PBLs were transduced with the TCR constructs and analyzed by tetramer staining and peptide-specific interferon-(IFN-)γ secretion. Both TCRs similarly bound the MHC-presented gp100-antigen as seen in comparable MFI in the staining with gp100-specific tetramer by flow cytometry (FIG. 9c). Upon stimulation with gp100 peptide-pulsed T2 cells, PBLs transduced with either TCR secreted comparable amounts of IFN-γ in a peptide dose-dependent manner (FIG. 9d).

To show that gp100/TCRmyc-modified T cells can be eliminated, PBLs were transduced with gp100/TCRmyc retroviruses, enriched with a myc-specific antibody and restimulated. PBLs that were 85 to 99% positive for myc-expression were subjected to complement-mediated lysis or antibody-dependent cell-mediated cytotoxicity assay (ADCC). Depending on the assay, 31 to 65% of the gp100/TCRmyc-transduced cells were depleted in the presence of a myc-specific antibody whereas cells incubated without antibody showed only some unspecific lysis (FIG. 10).

The invention claimed is:

1. A human or mouse T-cell receptor (TCR) alpha chain fusion protein expressed on the surface of a T-cell, comprising:
    a) at least one epitope-providing amino acid sequence (epitope-tag), and
    b) the amino acid sequence of a human or mouse alpha chain of a TCR that is known to bind a specific antigen, wherein said epitope-tag is selected from
        a) an epitope-tag added to the N- terminus of said alpha chain,
        b) an epitope-tag inserted into a constant region of said alpha chain, and
        c) an epitope-tag replacing a number of amino acids in a constant region of said alpha chain.

2. The T-cell receptor (TCR) alpha chain fusion protein according to claim 1, wherein said epitope-tag has a length of between 6 to 15 amino acids.

3. The T-cell receptor (TCR) alpha chain fusion protein according to claim 1, wherein said fusion protein comprises two or more epitope-tags, either spaced apart or directly in tandem.

4. The T-cell receptor (TCR) alpha chain fusion protein according to claim 1, wherein said epitope-tag is selected from the group consisting of: a myc-tag, FLAG-tag, T7-tag, HA (hemagglutinin)-tag, His-tag, S-tag, GST-tag, and GFP-tag.

5. The T-cell receptor (TCR) alpha chain fusion protein according to claim 1, wherein said fusion protein has two myc-tag sequences that are attached to the N-terminus of an alpha TCR-chain.

6. A method for producing a fusion protein according to claim 1, comprising a chemical synthesis of said protein.

7. An isolated nucleic acid molecule encoding the fusion protein according to claim 1.

8. The nucleic acid molecule according to claim 7, wherein said molecule is selected from DNA, RNA, PNA, CNA, mRNA or mixtures thereof.

9. A vector comprising an isolated nucleic acid molecule encoding the fusion protein of claim 1.

10. An isolated host cell, transfected with a vector according to claim 9, wherein the host cell is a T-cell or a T-cell-precursor cell or a non-pluripotent stem cell.

11. The isolated host cell according to claim 10, wherein said host cell expresses on its surface
    (i) a human or mouse T-cell receptor (TCR) alpha chain fusion protein, comprising:
        a) at least one epitope-providing amino acid sequence (epitope-tag), and
        b) the amino acid sequence of a human or mouse alpha chain of a TCR that is known to bind a specific antigen,
        wherein said epitope-tag is selected from
        I) an epitope-tag added to the N- terminus of said alpha chain,
        II) an epitope-tag inserted into a constant region of said alpha chain, and
        III) an epitope-tag replacing a number of amino acids in a constant region of said alpha chain, or
    (ii) a TCR comprising the TCR alpha chain fusion protein of (i).

12. A pharmaceutical composition, comprising a fusion protein according to claim 1, a nucleic acid molecule according to claim 7, a vector according to claim 9 or an isolated host T-cell according to claim 11, together with a pharmaceutically acceptable carrier.

* * * * *

SEQUENCE LISTING

<160> NUMBER OF SEQ ID NOS: 7

<210> SEQ ID NO 1

<211> LENGTH: 325
<212> TYPE: PRT
<213> ORGANISM: Mus musculus

<400> SEQUENCE: 1

Met Ser Asn Thr Ala Phe Pro Asp Pro Ala Trp Asn Thr Thr Leu Leu
1               5                   10                  15

Ser Trp Val Ala Leu Phe Leu Leu Gly Thr Lys His Met Glu Ala Ala
            20                  25                  30

Val Thr Gln Ser Pro Arg Ser Lys Val Ala Val Thr Gly Gly Lys Val
        35                  40                  45

Thr Leu Ser Cys His Gln Thr Asn Asn His Asp Tyr Met Tyr Trp Tyr
    50                  55                  60

Arg Gln Asp Thr Gly His Gly Leu Arg Leu Ile His Tyr Ser Tyr Val
65                  70                  75                  80

Ala Asp Ser Thr Glu Lys Gly Asp Ile Pro Asp Gly Tyr Lys Ala Ser
                85                  90                  95

Arg Pro Ser Gln Glu Asn Phe Ser Leu Ile Leu Glu Leu Ala Ser Leu
            100                 105                 110

Ser Gln Thr Ala Val Tyr Phe Cys Ala Ser Ser Asp Ala Gly Gly Arg
        115                 120                 125

Asn Thr Leu Tyr Phe Gly Ala Gly Thr Arg Leu Ser Val Leu Glu Asp
    130                 135                 140

Leu Arg Asn Val Thr Pro Pro Lys Val Ser Leu Phe Glu Pro Ser Lys
145                 150                 155                 160

Ala Glu Ile Ala Asn Lys Gln Lys Ala Thr Leu Val Cys Leu Ala Arg
                165                 170                 175

Gly Phe Phe Pro Asp His Val Glu Leu Ser Trp Trp Val Asn Gly Lys
            180                 185                 190

Glu Val His Ser Gly Val Ser Thr Asp Pro Gln Ala Tyr Lys Glu Ser
        195                 200                 205

Asn Tyr Ser Tyr Cys Leu Ser Ser Arg Leu Arg Val Ser Ala Thr Phe
    210                 215                 220

Trp His Asn Pro Arg Asn His Phe Arg Cys Gln Val Gln Phe His Gly
225                 230                 235                 240

Leu Ser Glu Glu Gln Lys Leu Ile Ser Glu Glu Asp Leu Gly Gln Lys
                245                 250                 255

Leu Ile Ser Glu Glu Asp Leu Pro Val Thr Gln Asn Ile Ser Ala Glu
            260                 265                 270

Ala Trp Gly Arg Ala Asp Cys Gly Ile Thr Ser Ala Ser Tyr His Gln
        275                 280                 285

Gly Val Leu Ser Ala Thr Ile Leu Tyr Glu Ile Leu Leu Gly Lys Ala
    290                 295                 300

Thr Leu Tyr Ala Val Leu Val Ser Gly Leu Val Leu Met Ala Met Val
305                 310                 315                 320

Lys Lys Lys Asn Ser
                325

<210> SEQ ID NO 2
<211> LENGTH: 296
<212> TYPE: PRT
<213> ORGANISM: Mus musculus

<400> SEQUENCE: 2

Met Asp Lys Ile Leu Thr Ala Ser Phe Leu Leu Leu Gly Leu His Leu
1               5                   10                  15

Ala Gly Val Asn Gly Glu Gln Lys Leu Ile Ser Glu Asp Leu Glu
            20                  25                  30

Gln Lys Leu Ile Ser Glu Glu Asp Leu Gln Gln Lys Glu Lys His Asp
        35                  40                  45

Gln Gln Gln Val Arg Gln Ser Pro Gln Ser Leu Thr Val Trp Glu Gly
50                  55                  60

Gly Thr Thr Val Leu Thr Cys Ser Tyr Glu Asp Ser Thr Phe Asn Tyr
65                  70                  75                  80

Phe Pro Trp Tyr Gln Gln Phe Pro Gly Glu Gly Pro Ala Leu Leu Ile
                85                  90                  95

Ser Ile Leu Ser Val Ser Asp Lys Lys Glu Asp Gly Arg Phe Thr Thr
            100                 105                 110

Phe Phe Asn Lys Arg Glu Lys Lys Leu Ser Leu His Ile Ile Asp Ser
            115                 120                 125

Gln Pro Gly Asp Ser Ala Thr Tyr Phe Cys Ala Ala Leu Tyr Gly Asn
        130                 135                 140

Glu Lys Ile Thr Phe Gly Ala Gly Thr Lys Leu Thr Ile Lys Pro Asn
145                 150                 155                 160

Ile Gln Asn Pro Glu Pro Ala Val Tyr Gln Leu Lys Asp Pro Arg Ser
                165                 170                 175

Gln Asp Ser Thr Leu Cys Leu Phe Thr Asp Phe Asp Ser Gln Ile Asn
            180                 185                 190

Val Pro Lys Thr Met Glu Ser Gly Thr Phe Ile Thr Asp Lys Thr Val
        195                 200                 205

Leu Asp Met Lys Ala Met Asp Ser Lys Ser Asn Gly Ala Ile Ala Trp
210                 215                 220

Ser Asn Gln Thr Ser Phe Thr Cys Gln Asp Ile Phe Lys Glu Thr Asn
225                 230                 235                 240

Ala Thr Tyr Pro Ser Ser Asp Val Pro Cys Asp Ala Thr Leu Thr Glu
                245                 250                 255

Lys Ser Phe Glu Thr Asp Met Asn Leu Asn Phe Gln Asn Leu Ser Val
            260                 265                 270

Met Gly Leu Arg Ile Leu Leu Leu Lys Val Ala Gly Phe Asn Leu Leu
        275                 280                 285

Met Thr Leu Arg Leu Trp Ser Ser
290                 295

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 8
<212> TYPE: PRT
<213> ORGANISM: Gallus gallus

<400> SEQUENCE: 4

Ser Ile Ile Asn Phe Glu Lys Leu
1               5

```
<210> SEQ ID NO 5
<211> LENGTH: 9
<212> TYPE: PRT
<213> ORGANISM: Lymphocytic choriomeningitis virus

<400> SEQUENCE: 5

Lys Ala Val Tyr Asn Phe Ala Thr Met
1               5

<210> SEQ ID NO 6
<211> LENGTH: 9
<212> TYPE: PRT
<213> ORGANISM: Homo sapiens

<400> SEQUENCE: 6

Ile Met Asp Gln Val Pro Phe Ser Val
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Gln Lys Leu Ile Ser Glu Glu Asp Leu
1               5                   10
```